US009677070B2

(12) United States Patent
Allison et al.

(10) Patent No.: US 9,677,070 B2
(45) Date of Patent: Jun. 13, 2017

(54) COMPOSITION AND METHOD FOR DIVERSIFICATION OF TARGET SEQUENCES

(71) Applicants: Omeros Corporation, Seattle, WA (US); University of Washington Through Its Center for Commercialization, Seattle, WA (US)

(72) Inventors: Daniel S. Allison, Lake Forest Park, WA (US); W. Jason Cummings, Bellevue, WA (US); John B. Leppard, Mukilteo, WA (US); Nancy Maizels, Seattle, WA (US); Larry W. Tjoelker, Kirkland, WA (US); Christi L. Wood, Snohomish, WA (US); Munehisa Yabuki, Seattle, WA (US)

(73) Assignees: Omeros Corporation, Seattle, WA (US); University of Washington Through Its Center for Commercialization, Seattle, WA (US)

(*) Notice: Subject to any disclaimer, the term of this patent is extended or adjusted under 35 U.S.C. 154(b) by 0 days.

(21) Appl. No.: 13/802,255

(22) Filed: Mar. 13, 2013

(65) Prior Publication Data
US 2013/0261012 A1  Oct. 3, 2013

Related U.S. Application Data

(60) Provisional application No. 61/611,446, filed on Mar. 15, 2012.

(51) Int. Cl.
| | |
|---|---|
| *C12N 15/85* | (2006.01) |
| *C12N 15/10* | (2006.01) |
| *C07K 16/00* | (2006.01) |
| *C07K 16/28* | (2006.01) |
| *C07K 16/30* | (2006.01) |
| *C12N 5/10* | (2006.01) |
| *C12N 15/13* | (2006.01) |
| *C12N 15/63* | (2006.01) |

(52) U.S. Cl.
CPC .......... *C12N 15/1082* (2013.01); *C07K 16/00* (2013.01); *C07K 16/2863* (2013.01); *C07K 16/30* (2013.01); *C07K 2317/24* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,946,778 A | 8/1990 | Ladner et al. | |
| 5,091,513 A | 2/1992 | Huston et al. | |
| 5,132,405 A | 7/1992 | Huston et al. | |
| 6,765,087 B1 | 7/2004 | Casterman et al. | |
| 6,838,254 B1 | 1/2005 | Hamers et al. | |
| 6,909,031 B2 | 6/2005 | Allen et al. | |
| 7,776,599 B2 | 8/2010 | Ohta et al. | |
| 8,609,818 B2 | 12/2013 | Leppard et al. | |
| 2002/0028488 A1 | 3/2002 | Singh et al. | |
| 2003/0182675 A1 | 9/2003 | Etches | |
| 2005/0216976 A1 | 9/2005 | Meagher et al. | |
| 2007/0186292 A1* | 8/2007 | Buerstedde et al. ............ 800/14 |
| 2009/0226421 A1 | 9/2009 | Parren et al. | |
| 2010/0093033 A1* | 4/2010 | Maizels et al. .............. 435/69.1 |

FOREIGN PATENT DOCUMENTS

| | | |
|---|---|---|
| EP | 1536004 | 6/2005 |
| EP | 1568765 A1 | 8/2005 |
| WO | WO 92/01047 | 1/1992 |
| WO | WO 93/11161 | 6/1993 |
| WO | WO 94/13804 | 6/1994 |
| WO | WO 01/59092 A2 | 8/2001 |

(Continued)

OTHER PUBLICATIONS

Reynaud et al., "Somatic Hyperconversion Diversifies the Single VH Gene of the Chicken with a High Incidence in the D Region" 59 Cell 171-183 (1989).*
Van Wyngaardt et al., "A large semi-synthetic single-chain Fv phage display libarary based on chicken immunloglobulin genes" 4 BMC Biotechnology 1-14 (2004).*
McCormack et al., "Avian B-Cell Development: Generation of an Immunoglobulin Repertoire by Gene Conversion" 219-241 (1991).*
Arakawa et al., "Immunoglobulin Gene Conversion: Insights From Bursal B Cells and the DT40 Cell Line" 229 Developmental Dynamics 458-464 (2004).*
Kanayama et al., "Genetic manipulation of an exogenous non-inmmunoglobulin protein by gene conversion machinery in a chicken B cell line" 34(2) Nucleic Acids Research e10 (2006).*
Maizels, N., "Immunoglobulin gene diversification,"*Annu. Rev. Genet.* 39:23-46 (2005).

(Continued)

*Primary Examiner* — Nancy H Leith
(74) *Attorney, Agent, or Firm* — Tineka J. Quinton; Marcia S. Kelbon

(57) ABSTRACT

The disclosure relates generally to the targeting of genes to, and their integration into, an immunoglobulin (antibody) heavy chain locus. In particular, the methods described herein contemplate replacing the single rearranged heavy chain V, D, and J genes of a B cell lymphoma such as DT40 with independently rearranged $V_H$-D-$J_H$ genes of chicken, in a system for generating immunoglobulin diversity. Also contemplated is replacement of the chicken $V_H$-D-$J_H$ with rearranged $V_H$-D-$J_H$ genes of other vertebrates including human in a system for generating immunoglobulin diversity, with the exception of any substitution disclosed and claimed in PCT application WO 2009/029315 A2. Also described is construction of a diverse chicken immunoglobulin heavy chain VDJ library in DT40 by homologous gene replacement of the single endogenous rearranged VDJ gene with a chicken VDJ repertoire using the described targeting vectors.

28 Claims, 8 Drawing Sheets

(56) References Cited

FOREIGN PATENT DOCUMENTS

| WO | WO 02/100998 A2 | 12/2002 |
|----|-----------------|---------|
| WO | WO 03/061363 A2 | 7/2003 |
| WO | WO 01/11644 A1 | 2/2004 |
| WO | WO 2006/079372 A1 | 8/2006 |
| WO | WO 2009/029315 A2 | 3/2009 |
| WO | WO 2010/037402 A1 | 4/2010 |
| WO | WO 2011/061937 A1 | 5/2011 |
| WO | WO 2012/122513 A2 | 9/2012 |

OTHER PUBLICATIONS

Sale, J.E., "Immunoglobulin diversification in DT40: a model for vertebrate DNA damage tolerance," *DNA Repair* 3:693-402 (2004).
Arakawa, H., et al., "Immunoglobulin gene conversion: Indights from bural B cells and the DT40 cell line," *Developmental Dynamics* 229:458-464 (2004).
Cummings, W. Jason, et al., "Chromatic structure regulates gene conversion," *PLoS Biology* 5(10):e246 (2007).
Yabuki, M., et al., "The MRE11-RAD50-NBSI complex accelerates somatic hypermutation and gene conversion of immunoglobulin variable regions," *Nature Immunology* 6(7):730-736 (2005).
Rada, C., et al., "AID-GFP chimeric protein increases hypermutation of Ig genes with no evidence of nuclear localization," *PNAS* 99(10):7003-7008 (2002).
Faili, A., et al., "ADI-dependent somatic hypermutation occurs as a DNA single-strand event in the BL2 cell line," *Nature Immunology* 3(9):815-821 (2002).
Martin, A., at al., "Activation-induced cytidine deaminase turns on somatic hypermutation in hybridomas," *Nature* 415:802-806 (2002).
Martin, A., et al., "AID and mismatch repair in antibody diversification," *Immunology* 2:605-914 (2002).
Winkles, J., "The TWEAK-Fn14 cytokine-receptor axis; discovery, biology and therapeutic targeting," *Nat Rev Drug Discov* 7(5):411-425 (2008).
Barbas, S., et al., "Human autoantibody recognition of DNA,"*Proc. Natl. Acad. Sci. USA* 92:2529-2533 (1995).
McLane, K., et al., "Transplantation of a 17-amino acid α-helical DNA-binding domain into an antibody molecule confers sequence-dependent DNA recognition," *Proc. Natl. Acad. Sci. USA* 92:5214-5218 (1995).
Klimka, A., et al., "Human anti-CD30 recombinant antibodies by guided phage antibody selection using cell panning," *Br. J. Cancer* 83(2):252-260 (2000).
Rader, C., et al., "A phage display approach for rapid antibody humanization: Designed combinatorial V gene libraries," *Proc. Natl. Acad. Sci. USA* 95:8910-8915 (1998).
Cumbers, S. J., et al., "Generatin and interative affinity maturation of antibodies in vitro using hypermutating B-cell lines," *Nature Biotechnology* 20:1129-1134 (2002).
Yabuki, M., et al., "E2A acts in cis in $G_1$ phase of cell cycle to promote Ig gene diversification," *J Immunol* 182:408-415 (2009).
Marks, J.D., et al., "By-passing immunization: Building high affinity human antibodies cy chain shuffling," *Biotechnology* 10:779-783 (1992).
Beibor, S.H.W., et al., "Guided selection of a pan carcinoma specific antibody reveals similar binding characteristics yet structural divergence between the original murine antibody and its human equivalent," *J. Mol. Biol.* 296:833-849 (2000).
Tsurushita, N., et al., "Humanization of a chicken anti-IL-12 monoclonal antibody," *J Immunological Methods* 295:9-19 (2004).
Seo, H., et al., "Rapid generation of specific antibodies by enhanced homologous recomibation," *Nature Biotechnology* 23(6):731-735 (2005).
Nishibori, N., et al., "Humanization of chicken monoclonal antibody using phase-display system," *Molecular Immunobiology* 43:634-642 (2006).
Barbas, S.M., et al., "Recognition of DNA by synthetic antibodies," *J. Am. Chem. Soc.* 116:2161-2162 (1994).

Cummings, W.J., et al., "Genetic variation stimulated by epigenetic modification," *PLos ONE* 3(12):e4075 (2007).
Gallia, G. L., et al., "Evaluation of an autoregulatory tetracycline regulated system," *Oncogene* 16:1879-1884 (1998).
Verschure, P.J., et al., "In vivo HP1 targeting causes large-scale chromatin condensation and enhanced histone lysine methylation," *Molecular and Cellular Biology* 25(11):4552-4564 (2005).
Tagami, H., et al., "Histone H3.1 and H3.3 complexes mediate nucleosome assembly pathways dependent or independent of DNA synthesis," *Cell* 116:51-61 (2004).
Schwager, J., et al., "Evolution of immunoglobulin light chain genes: analysis of *Xenopus* IgL isotypes and their contribution to antibody diversity," *The EMBO Journal* 10(3):505-511 (1991).
Ohta, K., et al., "A method for rapid generation of specific antibodies based on a new principle," *Biotechnology Journal* 6(1):77-80 (2006) (Japanese language).
Ohta, K., et al., "A method for rapid generation of specific antibodies based on a new principle," *Biotechnology Journal* 6(1):77-80 (2006) (English language translation of ABO0039).
Seo, H., et al., "Enahancement of homologous recombination of immunoglobulin locus and its application," 27th Japan Molecular Biology Association Annual Meeting, Program and Lecture P.365 W20-7 (2004), (Abstract only) (Japanese language).
Seo, H., et al., "Enahancement of homologous recombination of immunoglobulin locus and its application," 27th Japan Molecular Biology Association Annual Meeting, Program and Lecture P.365 W20-7 (2004). (Abstract only) (English language translation of ABO0040).
Seo, H., et al., "A method for rapid generation of monoclonal antibodies by activating homologous recombination," *Cell Engineering* 24(8):834-835 (2005). (Japanese language).
Seo, H., et al., "A method for rapid generation of monoclonal antibodies by activating homologous recombination," *Cell Engineering* 24(8):834-835 (2005). (English language translation of ABO0041).
Arakawa, H., et al., "Requirement of the activation-induced deaminase (AID) gene for immunoglobulin gene conversion," *Science* 295(5558):1301-1306 (2002).
Ohmori, H., et al., "A system for generation of antibodies and mutant proteins using a B cell line with an ON/OFF control device for hypermutation machinery," *Experimental Medicine* 24(9):1331-1335 (2006). (Japanese language).
Ohmori, H., et al., "A system for generation of antibodies and mutant proteins using a B cell line with an ON/OFF control device for hypermutation machinery," *Experimental Medicine* 24(9):1331-1335 (2006). (English language translation of ABO0043).
Todo, K., et al., "Novel in vitro screening system for monoclonal antibodies using hypermutating chicken B cell library," *J. Biosci. Bioeng.* 102(5):478-481 (2006).
Tumbar, T., et al., "Large-scale chromatin unfolding and remodeling induced by VP16 acidic activation domain," *J. Cell. Biol.* 145(7):1341-1354 (1999).
Seo, H., et al., "An ex vivo method for rapid generation of monoclonal antibodies (ADLib system)," *Nature Protocols* 1(3):1502-1506 (2006).
Lin, W., et al., "B-cell display-based one-step method to generate chimeric human IgG monoclonal antibodies," *Nucleic Acids Research* 39(3):e14 (2011).
Kanayama, N., et al., "Creation of valuable antibodies by an in Vitro antibody generation system using a hypermutating B cell line," *Yakugaku Zasshi* 129(1):11-17 (2009). English Abstract Only.
Yabuki, M., et al., "Antibody discovery Ex Vivo accelerated by the LacO/LacI regulatory network," *PLoS ONE* 7(4):e36032 (2012).
Barbas III, C.F., et al., "In vitro evolution of a neutralizing human antibody to human immunodeficiency virus type I to enhance affinity and broaden strain corss-reactivity," *Proc. Natl. Acad. Sci. USA* 91:3809-3813 (1994).
Carter, P., et al., "Humanization of an anti-p185$^{HER2}$ antibody for human cancer therapy," *Proc. Natl. Acad. Sci.* 89:4285-4289 (1992).
Chiarella, P., et al., "mouse monoclonal antibodies in biological research: strategies for high-throughput production," *Biotechnol Lett* 30:1303-1310 (2008).

(56) References Cited

OTHER PUBLICATIONS

Co, M.S., et al., "Humanized antibodies for antiviral therapy," *Proc. Natl. Acad. Sci. USA* 88:2869-2873 (1991).
Cubas, R., et al., "Trop2 expression contributes to tumor pathogenesis by activating the ERK MASPK pathway," *Molecular Cancer* 9:253 (2010).
Filmus, J., et al., "Glypicans," *Genome Biology* 9:224 (2008).
Gorman, S.D., et al., "Reshaping a therapeutic CD4 antibody," *Proc. Natl. Acad. Sci. USA* 88: 4181-4185 (1991).
Gram, H., et al., "In vitro selection and affinity maturation of antibodies from a naïve combinatorial immunoglobulin library," *Proc. Natl. Acad. Sci. USA* 89:3576-3580 (1992).
Grandea III, A.G., et al., "Human antibodies reveal a protective epitope that is highly conserved among human and nonhuman influenza A viruses," *PNAS* 107(28):12658-12663 (2010).
Hammond, P.W., "Accessing the human repertoire for broadly neutralizing HIV antibodies," *mAbs* 2(2):157-164 (2010).
Hatanaka, A., et al., "Similar effects of Brca2 truncation and Rad51 paralog deficiency on immunoglobulin V gene diversification in DT40 cells support an early role for Rad51 paralogs in homologous recombination," *Molecular and Cleeular Biology* 25(3):1124-1134 (2005).
Holliger, P., et al., ""Diabodies": Small bivalent and bispecific antibody fragments," *Proc. Natl. Acad. Sci. USA* 90:6444-6448 (1993).
Hu, S-Z., et al., "Minibody: A novel engineered enticarcinoembryonic antigen antibody fragment (single-chain Fv-$C_H3$) which exhibits rapid, high-level targeting of xenografts," *Cancer Research* 56:3055-3061 (1996).
Huston, J.S., et al., "Protein engineering of antibody binding sites: Recovery of specific activity in an anti-digoxin single-chain Fv analogue produced in *Escherichia coli,*" *Proc. Natl. Acad. Sci. USA* 85:5879-5883 (1988).
Ill, C.R., et al., "Design and construction of a hybrid immunoglobulin domain with properties of both heavy and light chain variable regions," *Protein Engineering* 10(8):949-957 (1997).
Inbar, D., et al., "Localization of antibody-combining sites within the variable portions of heavy and light chains," *Proc. Natl. Acad. Sci. USA* 69(9):2659-2662 (1972).
Katoh, M., "Networking of WNT, FGF, Notch, BMP, and Hedgehog signaling pathways during carcinogenesis," *Stem Cell Rev* 3:30-38 (2007).
LoBuglio, A.F., et al., "Mouse/human chimeric monoclonal antibody in man: kinetics and immune response," *Proc. Natl/ Acad. Sci. USA* 86:4220-4224 (1989).
Martin, F., et al., "The affinity-selection of a minibody polypeptide inhibitor of human interleukin-6," *The EMBO Journal* 13(22):5303-5309 (1994).
McConnell Smith, A., et al., "Generation of a nicking enzyme that stimulates site-specific gene conversion from the I-AniI LAGLIDADG homing endonuclease," *PNAS* 106(13):5099-5104 (2009).
Ordinario, E.C., et al., "RAD51 paralogs promote homology-directed repair at diversifying immunoglobulin V regions," *BMC Molecular Biology* 10:98 (2009).
Petrocca, F., et al., "Promise and challenge of RNA interference-based therapy for cancer," *J Clincal Oncology* 29(6):747-754 (2010).
Queen, C., et al., "A humanized antibody that binds to the interleukin 2 receptor," *Proc. Natl. Acad. Sci. USA* 86:10029-10033 (1989).
Ridgway, J.B.B., et al., "Knobs-into-holes" engineering of antibody $C_H3$ domains for heavy chain heterodimerization, *Protein Engineering* 9(7):617-621 (1996).
Robinett, C.C., et al., "In vivo localization of DNA sequences and visualization of large-scale chromatic organization using lac operator/repressor recognition," *The Journal of Cell Biology* 135(6):1685-1700 (1996).
Sato, K., et al., "Reshaping a human antibody to inhibit the interleukin 6-dependent tumor cell growth," *Cancer Research* 53:851-856 (1993).
Traunecker, A., et al., "Bispecific single chain molecules (Janusins) target cytotoxic lymphocytes on HIV infected cells," *The EMBO Journal* 10(12):3655-3659 (1991).
Wei, J., et al., "Canonical Wnt signaling induces skin fibrosis and subcutaneous lipoatrophy: a novel mouse model for scleroderma?" *Arthritis Rheum* 63(6):1707-1717 (2011).
Xu, J.L., et al., "Diversity in the CDR3 region of $V_H$ is sufficient for most antibody specificities," *Immunity* 13:37-45 (2000).
Ferrara, N., et al., "Pathways mediating VEGF-independent tumor angiogenesis," *Cytokine & Growth Factor Reviews* 21:21-26 (2010).
Almagro, J.C., et al., "Humanization of antibodies," *Fronteirs in Bioscience* 13:1619-1633 (2008).
Foote, J., et al., "Antibody framework residues affecting the conformation of the hypervariable loops," *J Mol Biol* 224:487-499 (1992).
Bratkovič, T., "Progress in the phage display: evolution of the technique and its applicatins," *Cell. Mol. Life Sci.* 67:749-767 (2010).
Reynaud, C-A., et al., "A hyperconversion mechanism generates the chicken light chain preimmune repertoire," *Cell* 48:379-388 (1987).
Shi, Q., et al., "siRNA therapy for cancer and non-lethal diseases such as arthritis and osteoporosis," *Expert Opin. Biol. Ther.* 11(1):5-16 (2011).
Huang, Z., et al., "Cancer stem cells in glioblastoma—molecular signaling and therapeutic targeting," *Protein Cell* 1(7):638-655 (2010).
Wang, X., et al., "Small interfering RNA for effective cancer therapies," *Mini-Reviews in Medicinal Chemistry* 11:114-124 (2011).
Kajita, M., et al., "Conditional transformation of immunoglobulin mutation pattern from gene conversion into point mutation by controlling XRCC3 expression in the DT40 B cell line," *J Biosci Bioengineer* 109(4):407-410 (2010).
Buerstedde, J-M., et al., "Increased ratio of targeted to random integration after transfection of chicken B cell lines," *Cell* 67:179-188 (1991).
Köhler, G., et al., "Continuous cultures of fused cells secreting antibody of predefined specificity," *Nature* 256:495-497 (1975).
Winter, G., et al., "Making antibodies by phage display technology," *Annu. Rev. Immunol.* 12:433-55 (1994).
Schier, R., et al., "Isolation of picomolar affinity anti-c-erbB-2 single-chain Fv by molecular evolution of the complementarity determining regions in the center of the antibody binding site," *J. Mo. Biol.* 263:551-567 (1996).
Portolano, S., et al., "Lack of promiscuity in autoantigen-specific h and L chain combinations as revealed by human H and L chain "roulette"," *The Journal of Immunology* 150(3):880-887 (1993).
Clackson, T., et al., "Making antibody fragments using phage display libraries," *Nature* 352:624-628 (1991).
Shaw, A.C., et al., "Mutations of immunoglobulin transmembrane and cytoplasmic domains: Effects on intracellular signaling and antigen presentation," *Cell* 63:381-392 (1990).
Riechmann, L., et al., "Reshaping human antibodies for therapy," *Nature* 332:323-327 (1988).
Verhoeyen, M., et al., "Reshaping human antibodies: Grafting an antilysozyme activity," *Science* 239:1534-1536 (1988).
Kettleborough, C.A., et al., "Humanization of a mouse monoclonal antibody by CDR-grafting: the importance of framework residues on loop conformation," *Protein Engineering* 4(7):773-873 (1991).
Maeda, H., et al., "Construction of reshaped human antibodies with HIV-neutralizing activity," *Hum Antibod Hybridomas* 2:124-134 (1991).
Co, M.S., et al., "Chimeric and humanized antibodies with specificity for the CD33 antigen," *The Journal of Immunology* 148(4):1149-1154 (1992).
Stemmer, W.P.C., "Rapid evolution of a protein in vitro by DNA shuffling," *Nature* 370:389-391 (1994).
Bird, R.E., et al., "Single-chain antigen-binding proteins," *Science* 242:423-426 (1988).

(56) References Cited

OTHER PUBLICATIONS

Ward, E.S., et al., "Binding activities of a repertoire of single immunoglobulin variable domains secreted from *Escherichia coli,*" *Nature* 341:544-546 (1989).
Reiter, Y.,et al., "Engineering antibody Fv fragments for cancer detection and therapy: disulfide-stabilized Fv fragments," *Nature Biotechnology* 14:1239-1245 (1996).
Hochman, J., et al., "Folding and interaction of subunits at the antibody combining sites," *Biochemistry* 15(12):2706-2710 (1976).
Ehrlich, P.H., et al., "Isolatin of an active heavy-chain variable domain from homogenous rabbit antibody by cathepsin B digestion of the aminoethylated heavy chain," *Biochemistry* 19:4091-4096 (1980).
Holliger, P., et al., "Engineering bispecific antibodies," *Current Opinion in Biotechnology* 4:446-449 (1993).
Tempest, P.R., et al., "Reshaping a human monoclonal antibody to inhibit human respiratory syncytial virus infection in vivo," *Biotechnology* 9:266-271 (1991).
Nijening, J.E., et al., "Using large-scale RNAi screens to identify novel drug targets for cancer," *IDrugs* 13(11):772-777 (2010).
Sale, J.E., et al., "Ablation of XRCC2/3 transforms immunoglobulin V gene conversion into somatic hypermutation," *Nature* 412:921-926 (2001).
Traunecker, A., et al., "Janusin: New molecular design for bispecific reagents," *Int. J. Cancer* 7:51-52 (1992).

\* cited by examiner

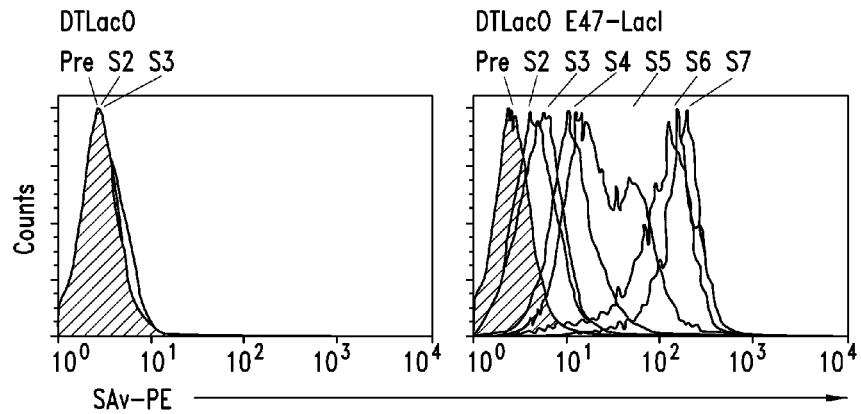

FIG. 3A

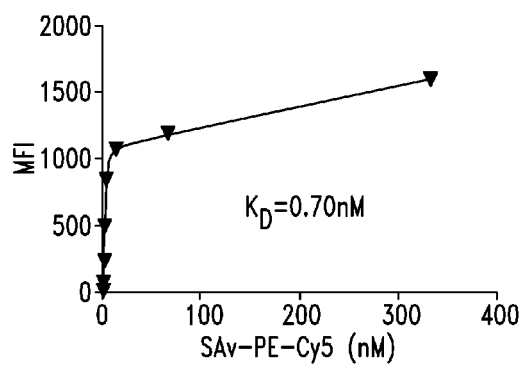

FIG. 3B

```
                 1                                                          60
V_H germline    AVTLDESGGGLQTPGRALSLVCKASGFTFS SYNMGW VRQAPGKGLEFVA GIDNTGRYTGY
SAv-PE S7       --------------G--------------- -NA--- ----------W-- ---DD-SG-R-

61                               101
V_H germline    GSA VKGRATISRDNGQSTVRLQLNNLRAEDTGTYYCAK AAG
SAv-PE S7       AP- ----------------L----------------T- C-Y 1                                                          60
V_λ germline    ALTQPSSVSANPGGTVKITC SGDSS              YYGW YQQKAPGSAPVTV
SAv-PE S7       -----A-------E------ -GG-YAGSYYYGWYQQKYAGSY---- ---S-------L 61                                                         112
V_λ germline    IY DNTNRPS NIPSRFSGSKSGSTATLTITGVRADDNAVYYC ASTDSSSTAAR
SAv-PE S7       -- N-N----D -----------------------E---F- G-A-N-GA-FG
```

FIG. 3C ent interest in this invention.

COMPOSITION AND METHOD FOR DIVERSIFICATION OF TARGET SEQUENCES

CROSS-REFERENCE TO RELATED APPLICATION

This application claims the benefit under 35 U.S.C. §119 (e) of U.S. Provisional Patent Application No. 61/611,446, filed Mar. 15, 2012, which application is incorporated herein by reference in its entirety.

STATEMENT OF GOVERNMENT INTEREST

This invention was made with government support under grants R01 GM41712 and U54 AI081680 awarded by the U.S. National Institutes of Health. The government has certain rights in this invention.

SEQUENCE LISTING

The Sequence Listing associated with this application is provided in text format in lieu of a paper copy, and is hereby incorporated by reference into the specification. The name of the text file containing the Sequence Listing is 980087_402_SEQUENCE_LISTING.txt. The text file is about 17 KB, was created on Jun. 4, 2013, and is being submitted electronically via EFS-Web.

BACKGROUND

Technical Field

This disclosure relates to the targeting of genes to, and their integration into, an immunoglobulin heavy chain locus. The vectors, compositions, and methods disclosed herein are particularly useful for ex vivo accelerated antibody evolution.

Description of the Related Art

Monoclonal antibodies (mAbs) are well-established as therapeutics, diagnostics, and reagents for research, but their use is currently limited by the difficulties and costs associated with identifying mAbs with the required affinity and specificity for a desired target. Many targets of interest are highly conserved proteins, and mechanisms of immune regulation limit the variety of antibodies that can be obtained from a physiological immune response. In addition, many key therapeutic targets are cell surface proteins, which present particular challenges to mAb development because their physiologically active conformations are not readily recapitulated by purified proteins or membrane preparations used for immunization to elicit specific antibodies. These cell surface components include some especially high value targets for certain clinically useful contexts, such as cytokine receptors and G protein-coupled receptors.

Most current strategies for mAb discovery employ in vivo and/or in vitro approaches. In vivo approaches involve activation and selection of specific antibody-producing B cells by immunization, followed by generation of hybridomas (Kohler et al., 1975; Chiarella et al., 2008). This process is costly and time-consuming, since extensive screening and, in many cases, subsequent steps including affinity maturation are required to obtain mAbs with desired properties. It is also limited by immune tolerance, making antibodies that specifically recognize some antigens difficult or impossible to obtain. In addition, once a mAb has been identified there is not a straightforward path to further optimization of its affinity or functionality. In vitro approaches often rely on screening massive numbers of synthetic single-chain antibodies, typically displayed on phage (Winter et al., 1994; Bratkovic et al., 2010). These antibodies are expressed by cloned genes that encode linked immunoglobulin heavy chain variable ($V_H$) and light chain variable ($V_L$) regions derived from an immune repertoire, often from a convalescent individual (Grandea et al., 2010; Hammond et al., 2010). They can be further optimized by iterative PCR-based mutagenesis accompanied by selection in vitro, using high throughput approaches. However, success in the end depends on the quality of the starting libraries and their sources, and not all single-chain antibodies can be readily converted to natural antibodies for practical applications.

mAb discovery can also be carried out ex vivo in immortalized B cells. B cells display immunoglobulin (Ig) molecules on the cell surface, facilitating selection for antigen recognition. In some B cell lines, physiological pathways for immunoglobulin (Ig) gene diversification remain active, enabling evolution of high affinity antibodies in culture. The chicken B cell line, DT40, has proven especially adaptable for such purposes (Cumbers et al., 2002; Seo et al., 2005; Kajita et al., 2010). DT40 derives from a bursal lymphoma, and DT40 cells constitutively diversify their immunoglobulin heavy chain variable region ($V_H$) and light chain variable region ($V_L$) genes (Arakawa et al., 2004). Ongoing diversification occurs by two pathways, gene conversion and somatic hypermutation (Maizels et al., 2005). Briefly, most mutations are templated and arise as a result of gene conversion, with nonfunctional pseudo-V regions serving as donors for the transfer of sequences to the rearranged and transcribed V gene. A small fraction of mutations are nontemplated, and arise as a result of somatic hypermutation, the mutagenic pathway that generates point mutations in Ig genes of antigen-activated human and murine B cells. DT40 cells proliferate rapidly, with an 8-10 hr doubling time (compared to 20-24 hr for human B cell lines), and are robust to experimental manipulations including magnetic-activated cell sorting (MACS), fluorescence-activated cell sorting (FACS) and single-cell cloning. Most importantly, DT40 cells support very efficient homologous gene targeting (Buerstedde et al., 1991), so genomic regions can in many cases be replaced or modified as desired using appropriately designed homologous recombination strategies.

Despite the considerable potential of DT40 cells for antibody evolution, their utility has thus far been limited in practice because—as in other transformed B cell lines—Ig gene diversification occurs at less than 1% the physiological rate. Several approaches have been used to accelerate diversification in DT40 cells. This can be achieved by disabling the homologous recombination pathway (Cumbers et al., 2002), but cells thus engineered have lost the ability to carry out gene targeting, or to diversify their Ig genes by gene conversion, and diversification produces nontemplated point mutations, like those generated during antigen-driven somatic hypermutation in humans or mice. Diversification can also be accelerated by treatment of cells with the histone deacetylase inhibitor, trichostatin A (Seo et al., 2005). This approach increases the rate of gene conversion, but does not promote point mutagenesis, limiting potential diversity. Clearly there remains a need for more rapid and effective generation of coding sequence diversity in a target gene of interest such as an antibody-encoding gene. The presently described compositions and methods address this need and offer other related advantages.

BRIEF SUMMARY

According to certain embodiments of the invention described herein there is provided a recombinant polynucleotide vector for integrating a target gene into a chicken immunoglobulin gene heavy chain locus, comprising (a) a chicken immunoglobulin $V_H$ gene upstream nucleic acid sequence region; (b) a target gene that comprises a rearranged chicken immunoglobulin $V_H$-D-$J_H$ gene that has been isolated from a population of chicken bursa of Fabricius cells; and (c) a chicken immunoglobulin $J_H$ gene downstream nucleic acid sequence region, wherein the target gene, upon being integrated into the chicken immunoglobulin heavy chain locus of a DT40 cell, is capable of undergoing either or both of (i) somatic hypermutation in an immunoglobulin $V_H$ region-encoding sequence, and (ii) gene conversion between a rearranged chicken immunoglobulin $V_H$-encoding nucleic acid sequence and a DT40 $V_H$ pseudogene nucleic acid sequence. In certain embodiments the target gene further comprises a polynucleotide sequence that encodes a marker protein, which in certain further embodiments is selected from green fluorescent protein (GFP) and blue fluorescent protein (BFP). In other embodiments the somatic hypermutation takes place in either or both of an immunoglobulin $V_H$ complementarity determining region-encoding sequence and an immunoglobulin $V_H$ framework region-encoding sequence.

In certain embodiments there is provided a composition comprising a plurality of recombinant polynucleotide vectors for integrating a plurality of target genes into a plurality of chicken immunoglobulin gene heavy chain loci, each of said vectors comprising (a) a chicken immunoglobulin $V_H$ gene upstream nucleic acid sequence region; (b) a target gene that comprises a rearranged chicken immunoglobulin $V_H$-D-$J_H$ gene that has been isolated from a population of chicken bursa of Fabricius cells; and (c) a chicken immunoglobulin $J_H$ gene downstream nucleic acid sequence region, wherein the target gene, upon being integrated into the chicken immunoglobulin heavy chain locus of a DT40 cell, is capable of undergoing either or both of (i) somatic hypermutation in an immunoglobulin $V_H$ region-encoding sequence, and (ii) gene conversion between the rearranged chicken immunoglobulin $V_H$-encoding nucleic acid sequence and a DT40 $V_H$ pseudogene nucleic acid sequence, and wherein the rearranged chicken immunoglobulin $V_H$-D-$J_H$ gene is obtained from a plurality of rearranged chicken immunoglobulin $V_H$-D-$J_H$ genes isolated from a population of chicken bursa of Fabricius cells. In certain embodiments the target gene further comprises a polynucleotide sequence that encodes a marker protein, which in certain further embodiments is selected from green fluorescent protein (GFP) and blue fluorescent protein (BFP). In certain embodiments the somatic hypermutation takes place in either or both of an immunoglobulin $V_H$ complementarity determining region-encoding sequence and an immunoglobulin $V_H$ framework region-encoding sequence.

In another embodiment there is provided a composition, comprising (a) the vector described above; and (b) a second vector for integrating a second target gene into an immunoglobulin gene light chain locus, the second vector comprising (1) a chicken immunoglobulin $V_L$ gene upstream nucleic acid sequence region; (2) a second target gene that comprises a rearranged chicken immunoglobulin $V_L$-$J_L$ gene that optionally has been isolated from a population of chicken bursa of Fabricius cells; and (3) a chicken immunoglobulin $J_L$ gene downstream nucleic acid sequence region, wherein the second target gene, upon being integrated into the chicken immunoglobulin light chain locus of a DT40 cell, is capable of undergoing either or both of (i) somatic hypermutation in an immunoglobulin $V_L$ region-encoding sequence, and (ii) gene conversion between a rearranged chicken immunoglobulin $V_L$-encoding nucleic acid sequence and a DT40 $V_L$ pseudogene nucleic acid sequence. In another embodiment there is provided a composition, comprising (1) the composition described above; and (2) one or a plurality of recombinant polynucleotide vectors for integrating a plurality of target genes into a plurality of chicken immunoglobulin gene light chain loci, each of said vectors comprising (a) a chicken immunoglobulin $V_L$ gene upstream nucleic acid sequence region; (b) a second target gene that comprises a rearranged chicken immunoglobulin $V_L$-$J_L$ gene optionally that has been isolated from a population of chicken bursa of Fabricius cells; and (c) a chicken immunoglobulin $J_L$ gene downstream nucleic acid sequence region, wherein the second target gene, upon being integrated into the chicken immunoglobulin light chain locus of a DT40 cell, is capable of undergoing either or both of (i) somatic hypermutation in an immunoglobulin $V_L$ region-encoding sequence, and (ii) gene conversion between a rearranged chicken immunoglobulin $V_L$-encoding nucleic acid sequence and a DT40 $V_L$ pseudogene nucleic acid sequence, and wherein optionally the rearranged chicken immunoglobulin $V_L$-$J_L$ gene is obtained from a plurality of isolated rearranged chicken immunoglobulin $V_L$-$J_L$ genes from a population of chicken bursa of Fabricius cells. In certain embodiments the second target gene further comprises a polynucleotide sequence that encodes a second marker protein, which in certain still further embodiments is selected from green fluorescent protein (GFP) and blue fluorescent protein (BFP). In certain embodiments the somatic hypermutation takes place in either or both of an immunoglobulin $V_L$ complementarity determining region-encoding sequence and an immunoglobulin $V_L$ framework region-encoding sequence.

Certain embodiments of the invention described herein provide a host cell, comprising any of the above described vectors or compositions. In certain embodiments the host cell is a bacterial cell. In certain embodiments the host cell is derived from a chicken cell, or is a chicken bursal lymphoma cell, or is a DT40 cell, and in certain further embodiments the immunoglobulin gene heavy chain locus in the host cell comprises a polymerized lactose operator and/or the immunoglobulin gene light chain locus in the host cell comprises a polymerized lactose operator. According to certain other embodiments there is provided a library of the herein described host cells.

Turning to another embodiment of the present invention, there is provided a method for integrating a target gene into a chicken immunoglobulin heavy chain locus, comprising (a) transfecting chicken B-cells with one of the above described vectors, or transfecting chicken B-cells with one of the above described compositions; and (b) identifying a chicken B-cell in which the target gene is integrated into the immunoglobulin heavy chain locus. In another embodiment there is provided a method for integrating a first target gene into a chicken immunoglobulin heavy chain locus and integrating a second target gene into an immunoglobulin light chain locus, comprising (a) transfecting one or a plurality of chicken B-cells with one of the above described compositions to obtain one or a plurality of transfected B-cells; and (b) identifying a transfected chicken B-cell from (a) in which the target gene that comprises a rearranged chicken immunoglobulin $V_H$-D-$J_H$ gene is integrated into the immunoglobulin gene heavy chain locus and the second target gene is integrated into the immunoglobulin gene light chain locus. In another embodiment there is provided a method for producing a repertoire of chicken immunoglobulin heavy chain polypeptide sequence variants of a target polypeptide that is encoded by a target gene that comprises a rearranged chicken immunoglobulin $V_H$-D-$J_H$ gene, comprising culturing a chicken B-cell containing one of the above described vectors under conditions that allow for proliferation of the B-cell until a plurality of B-cells is obtained, wherein the B-cell is capable of either or both of (i) somatic hypermutation in an immunoglobulin $V_H$ complementarity determining region-encoding sequence, and (ii) gene conversion between a rearranged chicken immunoglobulin $V_H$-encoding nucleic acid sequence and a $V_H$ pseudogene nucleic acid sequence, and thereby producing a repertoire of chicken immunoglobulin heavy chain polypeptide sequence variants of the target polypeptide. In certain related embodiments the chicken B-cell further comprises a second vector for integrating a second target gene into a chicken immunoglobulin gene light chain locus, the second vector comprising (a) a chicken immunoglobulin $V_L$ gene upstream nucleic acid sequence region; (b) a second target gene that comprises a rearranged chicken immunoglobulin $V_L$-$J_L$ gene optionally that has been isolated from a population of chicken bursa of Fabricius cells; and (c) a chicken immunoglobulin $J_L$ gene downstream nucleic acid sequence region, wherein the second target gene, upon being integrated into the chicken immunoglobulin light chain locus of a DT40 cell, is capable of undergoing either or both of (i) somatic hypermutation in an immunoglobulin $V_L$ complementarity determining region-encoding sequence, and (ii) gene conversion between a rearranged chicken immunoglobulin $V_L$-encoding nucleic acid sequence and a DT40 $V_L$ pseudogene nucleic acid sequence. In certain further embodiments the chicken immunoglobulin gene light chain locus comprises a polymerized lactose operator. In certain other further embodiments the chicken cell is selected from DT40 and DTLacO. According to certain other embodiments, the above described methods further comprise screening the plurality of chicken B-cells for binding to an antigen.

These and other aspects and embodiments of the herein described invention will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet are incorporated herein by reference in their entirety, as if each was incorporated individually. Aspects and embodiments of the invention can be modified, if necessary, to employ concepts of the various patents, applications and publications to provide yet further embodiments.

BRIEF DESCRIPTION OF THE DRAWINGS

FIGS. 3A-3C show rapid evolution of anti-streptavidin (SAv) antibodies in DTLacO cells. (A) SAv binding profile of successive selected cell populations of DTLacO (left) or DTLacO E47-LacI (right) cells. Selection was carried out on average at weekly intervals. Cell numbers were plotted relative to SAv-PE fluorescent signal. Populations at successive rounds of selection are designated above peaks (S0-S7). "Pre" designates populations prior to any sorting (gray fill). (B) Saturation binding kinetics of DTLacO E47-LacI S7 population. (C) Sequences of high affinity selected anti-SAv mAb compared to the germline (Reynaud et al., 1987; Reynaud et al., 1989). Complementarity determining regions (CDRs) are identified by enclosure in boxes. The 18-residue insertion/duplication in CDR1 of $V_\lambda$ of the anti-SAv mAb recapitulated an insertion in light-chain CDR1 reported by others selecting anti-SAv mAbs from DT40 cells that had not undergone any genetic engineering (Seo et al., 2005). The germline VH and Vλ sequences are set forth in SEQ ID NOS:17 and 19, respectively. The VH and Vλ sequences of the anti-SAv mAb are set forth in SEQ ID NOS:18 and 20, respectively.

DETAILED DESCRIPTION

Figure 1:
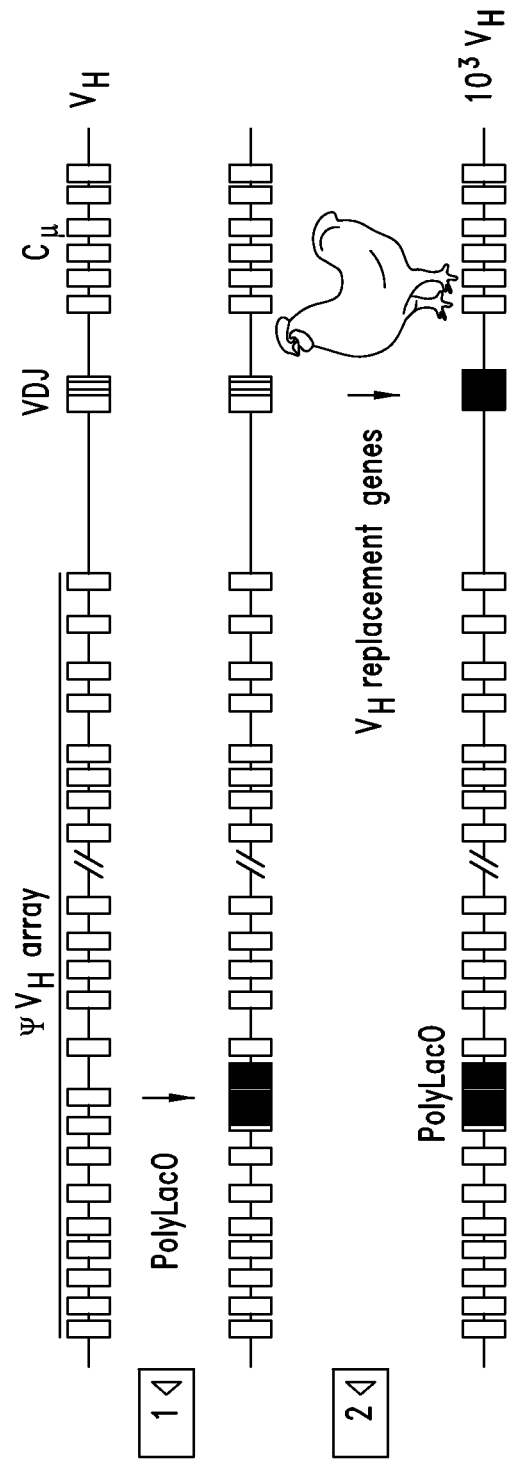
FIG. 1 shows schematic diagrams of two steps of engineering accelerated clonal diversification. The top schematic diagram shows the rearranged and expressed Ig heavy chain locus (IgH), containing the variable (VDJ) region, the constant ($C_\mu$) region, and the upstream $\psi V_H$ array. IgH was first modified by insertion of PolyLacO within the $\psi V_H$ array in DT40 PolyLacO-$\lambda_R$ cells, which carry PolyLacO targeted to the rearranged and expressed Ig light chain or λ locus (Igλ) (Cummings et al., 2007; Cummings et al., 2008; Yabuki et al., 2009). Next, this locus was further modified by substitution of the endogenous $V_H$ (VDJ) region with $V_H$ regions from a naive chick.

The present disclosure relates in part to recombinant polynucleotide vectors, and to related compositions, host cells, libraries and methods for integrating a target gene into a chicken immunoglobulin gene heavy chain locus. In particular, the methods described herein contemplate replacing a chicken immunoglobulin $V_H$-D-$J_H$ gene with a target gene via homologous recombination in a chicken B-cell. The chicken immunoglobulin gene heavy chain locus has been exceedingly difficult to characterize (see, Reynaud et al., Cell 59:171-83, 1989). Hence, successful integration of target genes into this locus could not previously have been predicted and has now surprisingly been achieved according to the disclosure found herein for the first time. The integration of target genes into this locus advantageously permits accelerated diversification of integrated target genes through either or both of somatic hypermutation and gene conversion in a chicken B-cell.

In a preferred embodiment, independently rearranged chicken immunoglobulin heavy chain variable ($V_H$) region, diversity (D) region and joining (J) region ($V_H$-D-$J_H$) genes (e.g., a $V_H$ library of already rearranged $V_H$-D-$J_H$ regions derived from a population of chicken bursa of Fabricius cells) are used to replace an endogenous chicken $V_H$-D-$J_H$ gene in a B cell lymphoma, such as DT40. Such replacement promotes accelerated generation of $V_H$ sequence diversity by the B-cells in combination with somatic hypermutation and gene conversion mechanisms. The methods disclosed herein are useful for generating a diverse library of immunoglobulins (Ig) that can be screened to identify and recover antibodies capable of specifically binding to desired target antigens.

Vectors

In certain embodiments, the present disclosure provides a recombinant polynucleotide vector for integrating a target gene into a chicken immunoglobulin gene heavy chain locus. The recombinant polynucleotide vector comprises: (a) a chicken immunoglobulin $V_H$ gene upstream nucleotide acid sequence region; (b) a target gene; and (c) a chicken immunoglobulin $J_H$ gene downstream nucleic acid sequence region. In a preferred embodiment, the target gene is a rearranged chicken immunoglobulin $V_H$-D-$J_H$ gene, which upon integration into the chicken immunoglobulin heavy chain locus of a DT40 cell, is capable of undergoing either or both of (i) somatic hypermutation in an immunoglobulin $V_H$ region-encoding sequence, and (ii) gene conversion between the rearranged chicken immunoglobulin $V_H$-encoding nucleic acid sequence and a DT40 $V_H$ pseudogene nucleic acid sequence. In certain embodiments the somatic hypermutation may occur in an immunoglobulin $V_H$ complementarity determining region (CDR)-encoding sequence, and in certain embodiments the somatic hypermutation may occur in an immunoglobulin $V_H$ framework region (FW)-encoding sequence and in certain embodiments the somatic hypermutation may occur in both an immunoglobulin $V_H$ complementarity determining region (CDR)-encoding sequence and an immunoglobulin $V_H$ framework region (FW)-encoding sequence.

A "recombinant polynucleotide vector" refers to a non-naturally occurring polynucleotide molecule useful for transferring coding information to a host cell. Such vectors are generated using DNA recombination techniques.

A "chicken immunoglobulin gene heavy chain locus" refers to the locus where a gene encoding the immunoglobulin heavy chain resides in the chicken genome. It contains a single $J_H$ gene and a unique functional $V_H$ gene 15 kb upstream, with approximately 15 D genes in between. See, Reynaud et al., Cell 59: 171-83, 1989. This locus also contains a cluster of pseudogenes ($\psi V_H$) spanning 60-80 kb, starting 7 kb upstream from the $V_H$ gene, as well as a cluster of C genes encoding immunoglobulin constant regions downstream of the $J_H$ gene.

The chicken immunoglobulin gene heavy chain locus has long been known as being unusually difficult to characterize or sequence (Reynaud et al., Cell 59: 171-83, 1989). Such difficulties may be due to GC-richness (i.e., a high frequency and preponderance of paired G-C dinucleotides) and/or to the presence of many repeated nucleotide sequences at this locus.

A "target gene" refers to a gene encoding a protein of interest. In a preferred embodiment, a target gene is a rearranged chicken immunoglobulin $V_H$-D-$J_H$ gene.

A "rearranged chicken immunoglobulin $V_H$-D-$J_H$ gene" refers to a chicken immunoglobulin $V_H$-D-$J_H$ gene rearranged in a somatic cell of the B-lymphocyte lineage so that the $V_H$, D, and $J_H$ genes are joined together rather than separated by other sequences, as in other cells. "Immunoglobulin $V_H$-D-$J_H$ gene" is used herein interchangeably with "Ig VDJ gene" or "immunoglobulin VDJ gene." In certain embodiments, the rearranged chicken immunoglobulin $V_H$-D-$J_H$ gene is isolated from a chicken bursa of Fabricius cell.

"Integrating a target gene into a chicken immunoglobulin gene heavy chain locus" refers to integrating a target gene into a chicken immunoglobulin gene heavy chain locus via homologous recombination. More specifically, such integration is accomplished by homologous recombination between an endogenous chicken immunoglobulin $V_H$-D-$J_H$ gene of a B-cell (e.g., a DT40 cell) and a recombinant polynucleotide vector that comprises both a chicken immunoglobulin $V_H$ gene upstream nucleic acid sequence region and a chicken immunoglobulin $J_H$ gene downstream nucleic acid sequence region. The vector further comprises the target gene between the chicken immunoglobulin $V_H$ gene upstream nucleic acid sequence region and the chicken immunoglobulin $J_H$ gene downstream nucleic acid sequence region.

A "chicken immunoglobulin $V_H$ gene upstream nucleic acid sequence region" refers to a region in a chicken genome that is upstream from the start codon (e.g., located 5' to the start codon when using the coding or sense strand for orientation) of a chicken immunoglobulin $V_H$ gene in certain embodiments. Such a region is also referred to as a "naturally occurring chicken immunoglobulin $V_H$ gene upstream nucleic acid sequence region." This region must be sufficiently long in a recombinant polynucleotide vector to allow for homogenous recombination with an endogenous $V_H$-D-$J_H$ gene of a chicken B-cell. In certain embodiments, this region is at least 100-2000 or at least 500-2000 (including all of the integers in the range, e.g., at least 100, at least 500, at least 1000, or at least 1500) nucleotides long. In certain embodiments, the 3'-terminus of the region is 1-1000 (including all the integers in this range) nucleotides from the start codon of a chicken immunoglobulin $V_H$ gene. In certain embodiments, a chicken immunoglobulin $V_H$ gene upstream nucleic acid sequence region does not include any sequences in the $\psi V_H$ array. In certain other embodiments, a chicken immunoglobulin $V_H$ gene upstream nucleic acid sequence region may include a sequence from the $\psi V_H$ array.

In certain other embodiments, a "chicken immunoglobulin $V_H$ gene upstream nucleic acid sequence region" may also include a sequence that is sufficiently homologous to a naturally occurring chicken immunoglobulin $V_H$ gene upstream nucleic acid sequence region to allow for homologous recombination with an endogenous $V_H$-D-$J_H$ gene of a chicken B-cell. Such regions may share at least 80.0-99.9 or at least 90.0-99.9 (including all of the values in the range, e.g., at least 80, at least 85, at least 90, at least 95, or at least 99) percent identity with a naturally occurring chicken immunoglobulin $V_H$ gene upstream nucleic acid sequence region.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers. In certain embodiments, the nucleotides comprising the polynucleotide can be ribonucleotides or deoxyribonucleotides or a modified form of either type of nucleotide. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, *Nucl. Acids Res.*, 14:9081; Stec et al., 1984, *J. Am. Chem. Soc.*, 106:6077; Stein et al., 1988, *Nucl. Acids Res.*, 16:3209; Zon et al., 1991, *Anti-Cancer Drug Design*, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, *Chemical Reviews*, 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell. The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

As will be understood by those skilled in the art, polynucleotides may include genomic sequences, extra-genomic and plasmid-encoded sequences and smaller engineered gene segments that express, or may be adapted to express, proteins, polypeptides, peptides and the like. Such segments may be naturally isolated, or modified synthetically by the skilled person.

As will also be recognized by the skilled artisan, polynucleotides may be single-stranded (coding or antisense) or double-stranded, and may be DNA (genomic, cDNA or synthetic) or RNA molecules. RNA molecules may include hnRNA molecules, which contain introns and correspond to a DNA molecule in a one-to-one manner, and mRNA molecules, which do not contain introns. Additional coding or non-coding sequences may, but need not, be present within a polynucleotide according to the present disclosure, and a polynucleotide may, but need not, be linked to other molecules and/or support materials. Polynucleotides may comprise a native sequence or may comprise a sequence that encodes a variant or derivative of such a sequence.

When comparing polynucleotide sequences, two sequences are said to be "identical" if the sequence of nucleotides in each of the two sequences is the same when the sequences are aligned for maximum correspondence. The percentage identity between two nucleotide sequences as described herein (e.g., with respect to a chicken immunoglobulin $V_H$ gene upstream nucleic acid sequence region and a chicken immunoglobulin JH gene downstream nucleic acid sequence region) may be determined according to art-accepted practices and criteria, for instance, the BLAST and BLAST 2.0 algorithms described in Altschul et al., *Nucl. Acids Res.* 25:3389-3402 (1977) and Altschul et al., *J. Mol. Biol.* 215:403-410 (1990), respectively. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extensions of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

A "chicken immunoglobulin $J_H$ gene downstream nucleic acid sequence region" refers to a region that is downstream from the splice site (e.g., located 3' to the splice site when using the coding or sense strand for orientation) of a chicken immunoglobulin $J_H$ gene in certain embodiments. Such a region is also referred to as a "naturally occurring chicken immunoglobulin $J_H$ gene downstream nucleic acid sequence region." This region must be sufficiently long in a recombinant polynucleotide vector to allow for homologous recombination with an endogenous $V_H$-D-$J_H$ gene of a chicken B-cell. In certain embodiments, this region is at least 100-2000 or at least 500-2000 (including all of the integers in the range, e.g., at least 100, at least 500, at least 1000, or at least 1500) nucleotides long. In certain embodiments, at least one of the 5' terminus of the region and the 3'-terminus of the region is 1-1000 (including all the integers in this range) nucleotides from the splice site of a chicken immunoglobulin $J_H$ gene. In certain embodiments, a chicken immunoglobulin $J_H$ gene downstream nucleic acid sequence region does not include any sequences in the cluster of C genes that encode constant regions of an immunoglobulin heavy chain.

In certain other embodiments, a "chicken immunoglobulin $J_H$ gene downstream nucleic acid sequence region" may also include a sequence that is sufficiently homologous to a naturally occurring chicken immunoglobulin $J_H$ gene downstream nucleic acid sequence region to allow for homologous recombination with an endogenous $V_H$-D-$J_H$ gene of a chicken B-cell. Such regions may share at least 80.0-99.9 or at least 90.0-99.9 (including all of the values in the range, e.g., at least 80, at least 85, at least 90, at least 95, or at least 99) percent identity with a naturally occurring chicken immunoglobulin $J_H$ gene downstream nucleic acid sequence region.

The DT40 chicken B-cell line is derived from an avian leukosis virus-induced bursal lymphoma. It is arrested at a bursal B-cell stage of differentiation and is known to constitutively mutate its heavy and light chain immunoglobulin genes in culture. Like other B cells, this constitutive mutagenesis targets mutations to the variable (V) region of immunoglobulin (Ig) genes, and thus, the complementarity determining regions (CDRs) of the expressed antibody molecules. Constitutive mutagenesis in DT40 cells takes place by gene conversion using as donor sequences an array of non-functional V genes (pseudo-V genes; ψV) situated upstream of each functional V region. Deletion of the ψV region at the light chain locus was previously shown to cause a switch in the mechanism of diversification from gene conversion to somatic hypermutation, the mechanism commonly observed in human B cells. DT40 has also been shown to support efficient homologous recombination, which enables the creation of modified cells in which specific genes are modified, deleted or inserted or where specific genes of interest replace an endogenous gene, in particular an endogenous rearranged Ig gene.

"Somatic hypermutation" refers to the mutation of a nucleic acid in a somatic cell at a rate above background (e.g., in a statistically significant manner). Preferably, hypermutation refers to a rate of mutation of between $10^{-5}$ and $10^{-3}$ bp$^{-1}$ generation$^{-1}$ at the physiological level. This is greatly higher than background mutation rates, which are of the order of $10^{-9}$ and $10^{-10}$ bp$^{-1}$ generation$^{-1}$. Somatic hypermutation may be detected by any suitable methods known in the art. For example, sequences of immunoglobulin heavy or light chain variable genes (e.g., complementarity determining region-encoding sequences of immunoglobulin heavy or light chain variable genes) from somatic cells (e.g., B-cells) may be compared to the most homologous germline variable gene sequence. In certain embodiments, sequences from somatic cells differ by at least 1-10 (including all of the integers in the range, e.g., at least 1, at least 2, at least 5, or at least 10) percent from their corresponding germline sequences.

"Gene conversion" refers to the transfer of sequence information in unidirectional manner from one homologous allele to the other. For example, gene conversion includes the process by which nonfunctional pseudo-V regions (e.g., $V_H$ or $V_L$ pseudogenes) serve as donors for transfer of a nucleotide sequence portion to the rearranged and transcribed V gene (e.g., rearranged and transcribed $V_H$ or $V_L$ genes). Gene conversion may be detected by any suitable methods known in the art, including comparing the sequences of rearranged V genes with those of pseudo-V regions.

Somatic hypermutation and gene conversion generate natural diversity within the immunoglobulin VDJ and VJ genes of B cells. Somatic hypermutation takes place in the germinal centers following antigen stimulation. Gene conversion takes place in primary lymphoid organs, like the bursa of Fabricius in chicken and other avian species, independent of antigen stimulation. In chicken, stretches from the upstream pseudo-V genes are transferred into the rearranged $V_H$-D-$J_H$ or $V_L$-$J_L$ gene.

In certain embodiments, the target gene may be a rearranged mammalian (e.g., human, mouse, or rabbit) immunoglobulin $V_H$-D-$J_H$ gene or a humanized immunoglobulin $V_H$-D-$J_H$ gene. By integrating the herein described composition into a chicken immunoglobulin gene heavy chain locus, the rearranged mammalian (e.g., human, mouse, or rabbit) immunoglobulin $V_H$-D-$J_H$ gene or the humanized immunoglobulin $V_H$-D-$J_H$ gene may be diversified via somatic hypermutation, gene conversion or both in a chicken B-cell, such as a DT40 cell.

In certain embodiments, the target gene does not include rearranged $V_H$-D-$J_H$ genes disclosed in PCT Application Publication No. 2009/029315.

In certain embodiments, the target gene is a gene encoding a marker protein, such as green fluorescent protein (GFP) and blue fluorescent protein (BFP). Additional exemplary genes include those encoding resistance to antibiotics such as neomycin, blasticidin, histidinol, hygromycin, zeocin, zeomycin, and puromycin. Additional exemplary target genes include rearranged $V_H$-D-$J_H$ genes fused with a coding sequence for a marker epitope such as a FLAG, Myc, or HA tag.

Recombinant polynucleotide vectors containing genes encoding marker proteins may be used to facilitate integration of other target genes in a chicken immunoglobulin heavy chain locus. For example, a recombinant polynucleotide vector comprising a chicken immunoglobulin $V_H$ gene upstream nucleic acid sequence region, a GFP gene, and a chicken immunoglobulin $J_H$ gene downstream nucleic acid sequence region may be used to first integrate the GFP gene into an immunoglobulin gene heavy chain locus of a chicken B-cell. Chicken B-cells with the GFP gene integrated can be easily detected based on the fluorescence generated by cellularly expressed GFP. Such B-cells can be then transfected with a second recombinant polynucleotide vector also comprising a chicken immunoglobulin $V_H$ gene upstream nucleic acid sequence region and a chicken immunoglobulin $J_H$ gene downstream nucleic acid sequence region but a second target gene (e.g., a rearranged chicken immunoglobulin $V_H$-D-$J_H$ gene). Via homologous recombination, the GFP gene may be replaced by the second target gene in some of the transfected B-cells, which cells may be easily detected by the loss of fluorescence produced by GFP.

In certain embodiments, the target gene is a gene encoding an enzyme of interest. The recombinant polynucleotide vector comprising such a target gene is helpful in diversifying the enzyme so that variants of the enzyme may be obtained that have modified properties (e.g., catalytic activity, substrate specificity, and/or heat stability). Exemplary target genes include those encoding receptors, ligands, proteases, lipases, glycosidases, phosphatases, kinases and nucleases.

In certain embodiments, recombinant polynucleotide vectors of the present disclosure comprise two or more target genes. For example, a recombinant polynucleotide vector that comprises a rearranged chicken immunoglobulin $V_H$-D-$J_H$ gene may further comprise another gene encoding a marker protein.

Recombinant polynucleotide vectors of the present disclosure may in certain embodiments contain one or more regulatory sequences, including promoter sequences, terminator sequences, polyadenylation sequences, enhancer sequences, marker genes and/or other sequences as appropriate. Vectors may be plasmids, viral, e.g. phage, or phagemid, as appropriate. For further details, see, for example, Molecular Cloning: a Laboratory Manual: 2nd edition, Sambrook et al., 1989, Cold Spring Harbor Laboratory Press. Many known techniques and protocols for manipulation of nucleic acid, such as preparing nucleic acid constructs, mutagenesis, sequencing, introduction of DNA into cells, etc. are described in detail in Current Protocols in Molecular Biology, Second Edition, Ausubel et al. eds., John Wiley & Sons, 1992, or subsequent updates thereto.

Compositions

The present disclosure also provides, according to certain embodiments, compositions that comprise the recombinant polynucleotide vectors disclosed herein.

In certain embodiments, there is provided a composition that comprises multiple recombinant polynucleotide vectors as disclosed herein. For instance, as disclosed herein such a composition may comprise a plurality of recombinant polynucleotide vectors for integrating a plurality of target genes into a plurality of chicken immunoglobulin gene heavy chain loci. Each of the vectors comprises: (a) a chicken immunoglobulin $V_H$ gene upstream nucleic acid sequence region; (b) a target gene; and (c) a chicken immunoglobulin $J_H$ gene downstream nucleic acid sequence region. The target genes in different vectors of the composition may have different nucleotide sequences and may encode one or a plurality of target proteins and/or one or more variants thereof.

A "variant" of a target protein" is a protein that has at least 60-99.5 (including all of the values in the above range, e.g., at least 60, at least 65, at least 70, at least 75, at least 80, at least 85, at least 90, at least 95, or at least 99) percent sequence homology with the target protein.

As used herein, percent homology of two amino acid sequences is also determined using BLAST programs of Altschul et al. (*J. Mol. Biol.* 215: 403-10, 1990) with their default parameters.

In a preferred embodiment, the target gene is a rearranged chicken immunoglobulin $V_H$-D-$J_H$ gene, which upon being integrated into the chicken immunoglobulin heavy chain locus of a DT40 cell, is capable of undergoing either or both of (i) somatic hypermutation in an immunoglobulin $V_H$-encoding sequence, which may include somatic hypermutation in an immunoglobulin $V_H$ complementartity determining region-encoding sequence and/or in an immunoglobulin $V_H$ framework region-encoding sequence, and (ii) gene conversion between the rearranged chicken immunoglobulin $V_H$-encoding nucleic acid sequence and a DT40 $V_H$ pseudogene nucleic acid sequence. In a further preferred embodiment, the rearranged chicken immunoglobulin $V_H$-D-$J_H$ gene is obtained from a plurality of rearranged chicken immunoglobulin $V_H$-D-$J_H$ genes isolated from a population of chicken bursa of Fabricius cells. The age of the chicken from which bursa of Fabricius cells are obtained may be embryonic day 15 through post-hatch day 180 (including all integers in the range). Rearranged chicken immunoglobulin $V_H$-D-$J_H$ genes isolated from chicken bursa of Fabricius cells may have already been diversified via somatic hypermutation and gene conversion in vivo. They may be further diversified when integrated again into chicken immunoglobulin heavy chain loci via the vectors provided herein.

According to certain embodiments described herein there is contemplated a composition that comprises multiple recombinant polynucleotide vectors for integrating multiple rearranged immunoglobulin $V_H$-D-$J_H$ genes into chicken immunoglobulin heavy chain loci. Such a composition is useful for preparing a library of immunoglobulin heavy chain variable regions, as described below.

In certain embodiments there is provided a composition that comprises a first recombinant polynucleotide vector for integrating a first target gene into a chicken immunoglobulin gene heavy chain locus as disclosed herein, and a second recombinant polynucleotide vector for integrating a second target gene into a chicken immunoglobulin gene light chain locus. The second recombinant polynucleotide vector comprises: (a) a chicken immunoglobulin $V_L$ gene upstream nucleic acid sequence region; (b) a second target gene; and (c) a chicken immunoglobulin $J_L$ gene downstream nucleic acid sequence region.

In a manner similar to that described above for the first target gene, the second target gene may be a gene encoding any protein of interest, such as immunoglobulins, marker proteins and enzymes.

In certain embodiments, the first and second target genes encode subunits of a protein or two proteins that bind to each other to form a protein complex. The composition in such embodiments is useful in diversifying both subunits or proteins to modify the characteristics (e.g., binding affinity or specificity) of resulting complexes. For example, the first target gene may encode an immunoglobulin heavy chain variable region (e.g., a mammalian (including human, mouse, or rabbit) or humanized immunoglobulin heavy chain variable region), and the second target gene may encode an immunoglobulin light chain variable region (e.g., a mammalian (including human, mouse, or rabbit) or humanized immunoglobulin light chain variable region). The composition in this example is useful in integrating both target genes into the genome of a chicken B-cell (e.g., DT40 cells) and diversifying both immunoglobulin heavy and light chain variable regions to develop immunoglobulin variable regions with altered affinity and/or specificity to an antigen.

In a preferred embodiment, the first target gene is a rearranged chicken immunoglobulin $V_H$-D-$J_H$ gene and the second target gene is a rearranged chicken immunoglobulin $V_L$-$J_L$ gene. Upon being integrated into the chicken immunoglobulin heavy chain locus of a DT40 cell, the first target gene is capable of undergoing either or both of (i) somatic hypermutation in an immunoglobulin $V_H$-encoding sequence, which may include somatic hypermutation in an immunoglobulin $V_H$ complementartity determining region-encoding sequence and/or in an immunoglobulin $V_H$ framework region-encoding sequence, and (ii) gene conversion between the rearranged chicken immunoglobulin $V_H$-encoding nucleic acid sequence and a DT40 $V_H$ pseudogene nucleic acid sequence; and the second target gene is capable of undergoing either or both of (i) somatic hypermutation in an immunoglobulin $V_L$-encoding sequence, which may include somatic hypermutation in an immunoglobulin $V_L$ complementartity determining region-encoding sequence and/or in an immunoglobulin $V_L$ framework region-encoding sequence, and (ii) gene conversion between the rearranged chicken immunoglobulin $V_L$-encoding nucleic acid sequence and a DT40 $V_L$ pseudogene nucleic acid sequence.

A "chicken immunoglobulin gene light chain locus" refers to the locus where a gene encoding the immunoglobulin light chain resides in the chicken genome. It contains a single $J_L$ gene and an upstream functional $V_L$ gene upstream. See, Reynaud et al., Cell 40: 283-91, 1985, U.S. Patent Application Publication No. US 2007/0186292, and PCT Application Publication No. WO 2009/029315. This locus also contains a cluster of pseudogenes ($\psi V_L$) upstream from the $V_L$ gene as well as a C gene encoding an immunoglobulin light chain constant region downstream of the $J_L$ gene.

A "rearranged chicken immunoglobulin $V_L$-$J_L$ gene" refers to a chicken immunoglobulin $V_L$-$J_L$ gene rearranged in a somatic cell of the B-lymphocyte lineage so that the $V_L$ and $J_L$ genes are joined together rather than separated by other sequences as in other cells (e.g., germline cells). "Immunoglobulin $V_L$-$J_L$ gene" is used herein interchangeably with "Ig VJ gene" or "immunoglobulin VJ gene." In certain embodiments, the rearranged chicken immunoglobulin $V_L$-$J_L$ gene is isolated from a chicken bursa of Fabricius cell.

"Integrating a target gene into a chicken immunoglobulin gene light chain locus" refers to integrating a target gene into a chicken immunoglobulin gene light chain locus via homologous recombination. More specifically, such integration is accomplished by homologous recombination between an endogenous chicken immunoglobulin $V_L$-$J_L$ gene of a B-cell (e.g., a DT40 cell) and a recombinant polynucleotide vector that comprises both a chicken immunoglobulin $V_L$ gene upstream nucleic acid sequence region and a chicken immunoglobulin $J_L$ gene downstream nucleic acid sequence region. The vector further comprises the target gene between the chicken immunoglobulin $V_L$ gene upstream nucleic acid sequence region and a chicken immunoglobulin $J_L$ gene downstream nucleic acid sequence region.

A "chicken immunoglobulin $V_L$ gene upstream nucleic acid sequence region" refers to a region in a chicken genome that is upstream from the start codon (e.g., located 5' to the start codon when using the coding or sense strand for orientation) of a chicken immunoglobulin $V_L$ gene in certain embodiments. Such a region is also referred to as a "naturally occurring chicken immunoglobulin $V_L$ gene upstream nucleic acid sequence region." This region must be sufficiently long in a recombinant polynucleotide vector to allow for homologous recombination with an endogenous $V_L$-$J_L$ gene of a chicken B-cell. In certain embodiments, this region is at least 100-2000 or at least 500-2000 (including all of the integers in the range, e.g., at least 100, at least 500, at least 1000, or at least 1500) nucleotides long. In certain embodiments, the 3'-terminus of the region is 1-1000 (including all the integers in this range) nucleotides from the start codon of a chicken immunoglobulin $V_L$ gene. In certain embodiments, a chicken immunoglobulin $V_L$ gene upstream nucleic acid sequence region does not include any sequences in the $\psi V_L$ array. In certain other embodiments, however, a chicken immunoglobulin $V_L$ gene upstream nucleic acid sequence region may include a sequence from the $\psi V_L$ array. For instance, certain $V_L$-targeted vectors may comprise a chicken immunoglobulin $V_L$ gene upstream nucleic acid sequence region that contains one, two or more $V_L$ pseudogenes in the upstream homology arm. As one example, a $V_L$-targeted vector contained two $V_L$ pseudogenes in the chicken immunoglobulin $V_L$ gene upstream nucleic acid sequence region as a result of the sequence distance (approximately 2.4 kb) between the $V_L$-encoding region and the nearest upstream $V_L$ pseudogene, which was a relatively short distance compared to the spacing between counterpart elements in the IgH locus.

In certain other embodiments, a "chicken immunoglobulin $V_L$ gene upstream nucleic acid sequence region" may also include a sequence that is sufficiently homologous to a naturally occurring chicken immunoglobulin $V_L$ gene upstream nucleic acid sequence region to allow for homologous recombination with an endogenous $V_L$-$J_L$ gene of a chicken B-cell. Such regions may share at least 80.0-99.9 or at least 90.0-99.9 (including all of the values in the range, e.g., at least 80, at least 85, at least 90, at least 95, or at least 99) percent identity with a naturally occurring chicken immunoglobulin $V_L$ gene upstream nucleic acid sequence region.

A "chicken immunoglobulin $J_L$ gene downstream nucleic acid sequence region" refers to a region that is downstream from the splice site (e.g., located 3' to the splice site when using the coding or sense strand for orientation) of a chicken immunoglobulin $J_L$ gene. Such a region is also referred to as a "naturally occurring chicken immunoglobulin $J_L$ gene downstream nucleic acid sequence region." This region must be sufficiently long in a recombinant polynucleotide vector to allow for homologous recombination with an endogenous $V_L$-$J_L$ gene of a chicken B-cell. In certain embodiments, this region is at least 100-2000 or at least 500-2000 (including all of the integers in the range, e.g., at least 100, at least 500, at least 1000, or at least 1500) nucleotides long. In certain embodiments, the 3'-terminus of the region is 1-1000 (including all the integers in this range) nucleotides from the splice site of a chicken immunoglobulin $J_L$ gene. In certain embodiments, a chicken immunoglobulin $J_L$ gene downstream nucleic acid sequence region does not include any sequences in the C gene that encode constant regions of an immunoglobulin light chain.

In certain other embodiments, a "chicken immunoglobulin $J_L$ gene downstream nucleic acid sequence region" may also include a sequence that is sufficiently homologous to a naturally occurring chicken immunoglobulin $J_L$ gene downstream nucleic acid sequence region to allow for homologous recombination with an endogenous $V_L$-$J_L$ gene of a chicken B-cell. Such regions may share at least 80.0-99.9 or 90.0-99.9 (including all of the values in the range, e.g., at least 80, at least 85, at least 90, at least 95, or at least 99) percent identity with a naturally occurring chicken immunoglobulin $J_L$ gene downstream nucleic acid sequence region.

According to certain other embodiments, the present disclosure provides a composition that comprises (1) a plurality of first recombinant polynucleotide vectors for integrating a plurality of first target genes into a plurality of chicken immunoglobulin gene heavy chain loci, and (2) a plurality of second recombinant polynucleotide vectors for integrating a plurality of second target genes into a plurality of chicken immunoglobulin gene light chain loci. Each of the first recombinant polynucleotide vectors comprises: (a) a chicken immunoglobulin $V_H$ gene upstream nucleotide acid sequence region; (b) a first target gene; and (c) a chicken immunoglobulin $J_H$ gene downstream nucleic acid sequence region. Each of the second recombinant polynucleotide vectors comprises: (a) a chicken immunoglobulin $V_L$ gene upstream nucleotide acid sequence region; (b) a second target gene; and (c) a chicken immunoglobulin $J_L$ gene downstream nucleic acid sequence region. The first target genes in different first recombinant polynucleotide vectors may have different nucleotide sequences and may encode a first target protein or its variants. Similarly, the second target genes in different second recombinant polynucleotide vectors may have different nucleotide sequences and may encode a second target protein or its variants.

In certain embodiments, the first and second target genes encode subunits of a protein or two proteins that bind to each other to form a protein complex or the variants of such subunits or proteins. For example, the first target gene may encode an immunoglobulin heavy chain variable region (e.g., a mammalian (including human, mouse, or rabbit) or humanized immunoglobulin heavy chain variable region), and the second target gene may encode an immunoglobulin light chain variable region (e.g., a mammalian (including human, mouse, or rabbit) or humanized immunoglobulin light chain variable region).

In a preferred embodiment, the first target gene is a rearranged chicken immunoglobulin $V_H$-D-$J_H$ gene and the second target gene is a rearranged chicken immunoglobulin $V_L$-$J_L$ gene. Upon being integrated into the chicken immunoglobulin heavy chain locus of a DT40 cell, the first target gene is capable of undergoing either or both of (i) somatic hypermutation in an immunoglobulin $V_H$ region-encoding sequence, which may include somatic hypermutation in an immunoglobulin $V_H$ complementartity determining region-encoding sequence and/or in an immunoglobulin $V_H$ framework region-encoding sequence, and (ii) gene conversion between the rearranged chicken immunoglobulin $V_H$-encoding nucleic acid sequence and a DT40 $V_H$ pseudogene nucleic acid sequence; and the second target gene is capable of undergoing either or both of (i) somatic hypermutation in an immunoglobulin $V_L$ region-encoding sequence, which may include somatic hypermutation in an immunoglobulin $V_L$ complementartity determining region-encoding sequence and/or in an immunoglobulin $V_L$ framework region-encoding sequence, and (ii) gene conversion between the rearranged chicken immunoglobulin $V_L$-encoding nucleic acid sequence and a DT40 $V_L$ pseudogene nucleic acid sequence. In a further preferred embodiment, the rearranged chicken immunoglobulin $V_H$-D-$J_H$ gene and/or the rearranged $V_L$-$J_L$ gene are obtained from a plurality of rearranged chicken immunoglobulin $V_H$-D-$J_H$ genes and/or rearranged $V_L$-$J_L$ genes isolated from a population of chicken bursa of Fabricius cells. The compositions comprising multiple first recombinant polynucleotide vectors and multiple second recombinant polynucleotide vectors are useful for generating a diverse library of immunoglobulins that can be screened for to identify and recover antibodies capable of specifically binding to desired target antigens as described below.

Antibodies and Antigen-Binding Fragments Thereof

An "antibody" is an immunoglobulin molecule capable of specific binding to a target, such as a carbohydrate, polynucleotide, lipid, polypeptide, etc., through at least one epitope recognition site, located in the variable region (also referred to herein as the variable domain) of the immunoglobulin molecule. As used herein, the term "antibody" encompasses not only intact polyclonal or monoclonal antibodies, but also fragments thereof (such as a single variable region antibody (dAb), or other known antibody fragments such as Fab, Fab', F(ab')$_2$, Fv and the like, single chain (ScFv), synthetic variants thereof, naturally occurring variants, fusion proteins comprising an antibody portion with an antigen-binding fragment of the required specificity, humanized antibodies, chimeric antibodies, and any other engineered or modified configuration of the immunoglobulin molecule that comprises an antigen-binding site or fragment (epitope recognition site) of the required specificity. "Diabodies", multivalent or multispecific fragments constructed by gene fusion (WO94/13804; Holliger et al, Proc. Natl. Acad. Sci. USA 90 6444-6448, 1993) are also a particular form of antibody contemplated herein. Minibodies comprising a scFv joined to a CH3 domain are also included herein (Hu et al, Cancer Res., 56, 3055-3061, 1996; see also e.g., Ward et al., Nature 341, 544-546 (1989); Bird et al, Science 242, 423-426, 1988; Huston et al, PNAS USA, 85, 5879-5883, 1988; PCT/US92/09965; WO94/13804; Holliger et al., Proc. Natl. Acad. Sci. USA 90 6444-6448, 1993; Reiter et al., Nature Biotech 14, 1239-1245, 1996; Hu et al, Cancer Res. 56, 3055-3061, 1996). Nanobodies and maxibodies are also contemplated (see, e.g., U.S. Pat. No. 6,765,087; U.S. Pat. No. 6,838,254; WO 06/079372; WO 2010/037402).

The term "antigen-binding fragment" as used herein refers to a polypeptide fragment that contains at least one CDR of an immunoglobulin heavy and/or light chain that binds to the antigen of interest. In this regard, an antigen-binding fragment of the herein described antibodies may comprise one, two, three, four, five or all six CDRs of a VH and/or VL sequence set forth herein.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, that is capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. In certain embodiments, an antibody is said to specifically bind an antigen when it preferentially recognizes its target antigen in a complex mixture of proteins and/or macromolecules. An antibody may according to certain embodiments be said to bind an antigen specifically when the equilibrium dissociation constant for antibody-antigen binding is less than or equal to $10^{-6}$M, or less than or equal to $10^{-7}$ M, or less than or equal to $10^{-8}$ M. In some embodiments, the equilibrium dissociation constant may be less than or equal to $10^{-9}$ M or less than or equal to $10^{-10}$ M.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule (Inbar et al. (1972) Proc. Nat. Acad. Sci. USA 69:2659-2662; Hochman et al. (1976) Biochem 15:2706-2710; and Ehrlich et al. (1980) Biochem 19:4091-4096).

In certain embodiments, single chain Fv or scFV antibodies are contemplated. For example, Kappa bodies (Ill et al., *Prot. Eng.* 10:949-57 (1997); minibodies (Martin et al., *EMBO J.* 13:5305-9 (1994); diabodies (Holliger et al., *PNAS* 90:6444-8 (1993)); or Janusins (Traunecker et al., *EMBO J.* 10:3655-59 (1991) and Traunecker et al. *Int. J. Cancer Suppl.* 7:51-52 (1992)), may be prepared using standard molecular biology techniques following the teachings of the present application with regard to selecting antibodies having the desired specificity. In still other embodiments, bispecific or chimeric antibodies may be made that encompass the ligands of the present disclosure. For example, a chimeric antibody may comprise CDRs and framework regions from different antibodies, while bispecific antibodies may be generated that bind specifically to a desired antigen through one binding domain and to a second molecule through a second binding domain. These antibodies may be produced through recombinant molecular biological techniques or may be physically conjugated together.

A single chain Fv (sFv) polypeptide is a covalently linked $V_H::V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

A dAb fragment of an antibody consists of a VH domain (Ward, E. S. et al., Nature 341, 544-546 (1989)).

In certain embodiments, an antibody as herein disclosed is in the form of a diabody. Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site; antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Holliger, P. and Winter G. *Current Opinion Biotechnol.* 4, 446-449 (1993)), e.g. prepared chemically or from hybrid hybridomas, or may be any of the bispecific antibody fragments mentioned above. Diabodies and scFv can be constructed without an Fc region, using only variable regions, potentially reducing the likelihood or severity of an elicited immune response, such as an anti-idiotypic reaction, in a subject receiving an administration of such antibodies.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (Ridgeway et al, *Protein Eng.*, 9, 616-621, 1996).

In certain embodiments, the antibodies described herein may be provided in the form of a UNIBODY®. A UNIBODY® is an IgG4 antibody with the hinge region removed (see GenMab Utrecht, The Netherlands; see also, e.g., US20090226421). This proprietary antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UNIBODY® that can bind to cognate antigens (e.g., disease targets) and the UNIBODY® therefore binds univalently to only one site on target cells. For certain cancer cell surface antigens, this univalent binding may not stimulate the cancer cells to grow as may be seen using bivalent antibodies having the same antigen specificity, and hence UNIBODY® technology may afford treatment options for some types of cancer that may be refractory to treatment with conventional antibodies. The UNIBODY® is about half the size of a regular IgG4 antibody. This small size can be a great benefit when treating some forms of cancer, allowing for better distribution of the molecule over larger solid tumors and potentially increasing efficacy.

In certain embodiments, the antibodies of the present disclosure may take the form of a nanobody. Nanobodies are encoded by single genes and are efficiently produced in almost all prokaryotic and eukaryotic hosts, e.g., *E. coli* (see e.g. U.S. Pat. No. 6,765,087), molds (for example *Aspergillus* or *Trichoderma*) and yeast (for example *Saccharomyces, Kluyvermyces, Hansenula* or *Pichia* (see e.g. U.S. Pat. No. 6,838,254)). The production process is scalable and multi-kilogram quantities of nanobodies have been produced. Nanobodies may be formulated as a ready-to-use solution having a long shelf life. The Nanoclone method (see, e.g., WO 06/079372) is a proprietary method for generating Nanobodies against a desired target, based on automated high-throughput selection of B-cells.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable regions may be determined by reference to Kabat, E. A. et al, Sequences of Proteins of Immunological Interest, 4th Edition, US Department of Health and Human Services, 1987, and updates thereof, now available on the Internet (immuno.bme.nwu.edu).

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above.

"Humanized" antibodies refer to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable regions fused onto constant domains or only the CDRs grafted onto appropriate framework regions in the variable domains. Epitope binding sites may be wild type or may be modified by one or more amino acid substitutions. This chimeric structure eliminates the constant region of non-human origin as an immunogen in human individuals, but the possibility of an immune response to the foreign variable region remains (LoBuglio, A. F. et al., (1989) Proc Natl Acad Sci USA 86:4220-4224; Queen et al., PNAS (1988) 86:10029-10033; Riechmann et al., Nature (1988) 332:323-327).

Another approach focuses not only on providing human-derived constant regions, but also on modifying the variable regions as well so as to reshape them as closely as possible to human form. As also noted above, it is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When non-human antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato, K., et al., (1993) Cancer Res 53:851-856; Riechmann, L., et al., (1988) Nature 332:323-327; Verhoeyen, M., et al., (1988) Science 239:1534-1536; Kettleborough, C. A., et al., (1991) Protein Engineering 4:773-3783; Maeda, H., et al., (1991) Human Antibodies Hybridoma 2:124-134; Gorman, S. D., et al., (1991) Proc Natl Acad Sci USA 88:4181-4185; Tempest, P. R., et al., (1991) Bio/Technology 9:266-271; Co, M. S., et al., (1991) Proc Natl Acad Sci USA 88:2869-2873; Carter, P., et al., (1992) Proc Natl Acad Sci USA 89:4285-4289; and Co, M. S. et al., (1992) J Immunol 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies of the present disclosure may be chimeric antibodies. In this regard, a chimeric antibody is comprised of an antigen-binding fragment of an antibody of desired binding specificity operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

In certain embodiments, an antibody having a desired antigen-binding specificity comprises one or more of the CDRs of the antibodies described herein. In this regard, it has been shown in some cases that the transfer of only the VHCDR3 of an antibody can be done while still retaining desired specific binding (Barbas et al., PNAS (1995) 92: 2529-2533). See also, McLane et al., PNAS (1995) 92:5214-5218, Barbas et al., J. Am. Chem. Soc. (1994) 116:2161-2162.

Marks et al (Bio/Technology, 1992, 10:779-783) describe methods of producing repertoires of antibody variable domains in which consensus primers directed at or adjacent to the 5' end of the variable domain area are used in conjunction with consensus primers to the third framework region of human VH genes, to provide a repertoire of VH variable domains lacking a CDR3. Marks et al further describe how this repertoire may be combined with a CDR3 of a particular antibody. Using analogous techniques, the CDR3-derived sequences of the presently described antibodies may be shuffled with repertoires of VH or VL domains lacking a CDR3, and the shuffled complete VH or VL domains combined with a cognate VL or VH domain to provide an antibody or antigen-binding fragment thereof that binds a desired antigen. The repertoire may then be displayed in a suitable host system such as the phage display system of WO92/01047 so that suitable antibodies or antigen-binding fragments thereof may be selected. A repertoire may consist of at least from about $10^4$ individual members and upwards by several orders of magnitude, for example, to about from $10^6$ to $10^8$ or $10^{10}$ or more members. Analogous shuffling or combinatorial techniques are also disclosed by Stemmer (Nature, 1994, 370:389-391), who describes the technique in relation to a β-lactamase gene but observes that the approach may be used for the generation of antibodies.

A further alternative is to generate novel VH or VL regions carrying one or more CDR-derived sequences of the herein described invention embodiments using random mutagenesis of one or more selected VH and/or VL genes to generate mutations within the entire variable domain. Such a technique is described by Gram et al. (1992 *Proc. Natl. Acad. Sci. USA* 89:3576-3580), who used error-prone PCR. Another method which may be used is to direct mutagenesis to CDR regions of VH or VL genes. Such techniques are disclosed by Barbas et al. (1994 *Proc. Natl. Acad. Sci. USA* 91:3809-3813) and Schier et al. (1996 *J. Mol. Biol.* 263: 551-567).

In certain embodiments, a specific VH and/or VL of the antibodies described herein may be used to screen a library of the complementary variable domain to identify antibodies with desirable properties, such as increased affinity for a desired antigen. Such methods are described, for example, in Portolano et al., *J. Immunol.* (1993) 150:880-887; Clarkson et al., *Nature* (1991) 352:624-628.

Other methods may also be used to mix and match CDRs to identify antibodies having desired binding activity. For example: Klimka et al., *British Journal of Cancer* (2000) 83: 252-260, describe a screening process using a mouse VL and a human VH library with CDR3 and FR4 retained from the mouse VH. After obtaining antibodies, the VH was screened against a human VL library to obtain antibodies that bound antigen. Beiboer et al., *J. Mol. Biol.* (2000) 296:833-849 describe a screening process using an entire mouse heavy chain and a human light chain library. After obtaining antibodies, one VL was combined with a human VH library with the CDR3 of the mouse retained. Antibodies capable of binding antigen were obtained. Rader et al., *Proc. Nat. Acad. Sci. USA* (1998) 95:8910-8915 describe a process similar to that of Beiboer et al above.

These just-described techniques are, in and of themselves, known as such in the art. Based on the present disclosure, the skilled person will, however, be able to use such techniques to obtain antibodies or antigen-binding fragments thereof according to several embodiments of the invention described herein, using routine methodology in the art.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) *Annual Rev. Biochem.* 59:439-473.

The term "immunologically active", with reference to an epitope being or "remaining immunologically active", refers to the ability of an antibody to bind to the epitope under different conditions, for example, after the epitope has been subjected to reducing and denaturing conditions.

Host Cells and Libraries

In other embodiments, the present disclosure provides host cells that comprise the recombinant polynucleotide vectors or compositions that comprise such vectors disclosed herein.

In certain related embodiments, the host cells are capable of propagating the herein described recombinant polynucleotide vectors. Exemplary host cells for such purposes include bacterial cells (e.g., *E. coli*)

In certain embodiments, the host cells are chicken cells that permit integration of a target gene into a chicken immunoglobulin gene heavy or light chain locus. In a preferred embodiment, the host cells are chicken B-cells or cells derived from chicken B-cells, such as chicken bursal lymphoma cells. In a further preferred embodiment, the host cells are DT40 cells.

In certain embodiments, the host cells are chicken B-cells (e.g., DT40 cells) that further comprise a "cis-regulatory element" (e.g., a polymerized lactose operator sequence) in their immunoglobulin gene heavy chain loci and/or their immunoglobulin gene light chain loci to allow for the use of the systems described in WO 2009/029315 and US 20100093033 that further facilitate diversifying target sequences. Briefly, therein is described a modified B cell that permits reversible induction of diversification of a target gene. The cells are modified to include a "cis-regulatory element" operably linked to a target gene of interest (e.g., a rearranged chicken immunoglobulin $V_H$-D-$J_H$ gene). The cell is further modified to include a "diversification factor" that is fused to a "tethering factor." The function of the tethering factor is to bind to the cis-regulatory element, thereby bringing the diversification factor to the region that controls expression and/or mutagenesis of the target gene. The role of the diversification factor is to accelerate or regulate diversification (mutation) of the target sequence. Since the target gene is inserted into an Ig locus, mutations are targeted to its coding region and controlled by the use of the diversification factor-tethering factor fusion protein. Generally, the cis-regulatory element may be any DNA sequence that allows binding of a tethering factor thereto in a sequence-specific manner and is positioned in a region that controls expression or diversification of a gene (e.g., the gene of interest, such as a target gene). The cis-regulatory elements may include a polymerized Lactose operator (PolyLacO), such as those comprising approximately 100 repeats of the 20 base pair LacO binding site. The cis-regulatory element is positioned within the ψV region of the IgA light chain and the IgH loci. The tethering factor includes the Lac repressor (LacI) that binds with high affinity to the LacO. This insertion of the cis-regulatory element does not affect the normal process of templated mutagenesis (gene conversion) in the modified DT40 cell line.

The inducible aspect of the system of WO2009029315 and US2010093033 occurs through expression of tethering factor (LacI)-diversification factor fusion proteins and the use of isopropyl β-D-1-thiogalactopyranoside (IPTG), a small molecule which causes release of LacI from LacO. Culture of the modified DT40 cells with as little as 10 μM IPTG causes release of LacI from the PolyLacO and does not affect cell proliferation. Many different diversification factors are contemplated and include factors that affect chromatin structure, transcriptional activators and other gene regulators, deaminases, proteins involved in DNA repair and replication, resolvases and helicases, cell cycle regulators, proteins of the nuclear pore complex, and proteins involved in ubiquitinylation. An exemplary tethering factor-diversification factor construct includes LacI-HP1. In this construct, the heterochromatin protein, HP1, promotes a closed chromatin structure of neighboring genes. Thus, when LacI is bound to the PolyLacO in the modified DT40 cells, the tethered HP1 protein causes a transition of the donor ψV sequences from an open to a nonpermissive chromatin state. This is functionally equivalent to the deletion of the ψV region and similarly results in the switch from a templated mutagenesis of the downstream Ig Vλ locus to a somatic hypermutation of this targeted region. Additional tethering factor-diversification factor constructs useful in combination with PolyLacO are also described in WO2009029315 and US2010093033.

In certain embodiments, the host cells are chicken cells (e.g., DT40 cells) in which genes encoding chicken Ig heavy chain constant regions and/or genes encoding chicken Ig light chain constant regions have been replaced with genes encoding human Ig heavy and/or light chain constant regions. Such replacements may also be made via homologous recombination at regions upstream and downstream from the chicken genes to be replaced. Such host cells are capable of generating chimeric antibodies and thus facilitating the humanization of desirable antibodies produced in those cells.

In a related embodiment, the present disclosure provides libraries of host cells that comprise the herein described recombinant polynucleotide vectors.

In one embodiment, a library of host cells for propagating recombinant polynucleotide vectors disclosed herein is provided. For example, a bacterial cell library may be made by transforming bacterial cells with a composition comprising multiple recombinant polynucleotide vectors for integrating rearranged chicken immunoglobulin $V_H$-D-$J_H$ genes isolated from chicken bursa of Fabricius cells. Similarly, another bacterial cell library may be made by transforming bacterial cells with a composition comprising multiple recombinant polynucleotide vectors for integrating rearranged chicken immunoglobulin $V_L$-$J_H$ genes isolated from chicken bursa of Fabricius cells.

In another embodiment, there is provided a library of chicken cells with target genes integrated into their immunoglobulin gene heavy and/or light chain loci. An exemplary library may comprise DT40 cells transfected with recombinant polynucleotide vectors that contain different heavy chain variable region genes isolated from bursa of Fabricius cells from one or more chickens. Such a library may be made according to the method for integrating target genes into chicken immunoglobulin heavy and/or light chain loci as described herein.

In a further embodiment, provided is a library of chicken cells with target genes integrated into their immunoglobulin gene heavy and/or light chain loci and further diversified. An exemplary library may comprise progeny of DT40 cells transfected with recombinant polynucleotide vectors that contain different Ig heavy chain variable region genes isolated from bursa of Fabricius cells from one or more chickens. They may be made according to the method for producing repertoires of chicken immunoglobulin heavy and/or light chain polypeptide sequence variants as described herein.

The libraries provided herein may comprise at least $10$-$10^{14}$ (including all of the integers in the above range, e.g., at least 10, at least 100, at least 1000, at least 10,000, at least $10^5$, $10^6$, $10^7$, $10^8$, $10^9$, $10^{10}$, etc.) cells containing sequence variants of target genes, for example, in certain embodiments at least $10^3$-$10^7$ cells containing sequence variants of target genes. For instance, a library may have at least $10$-$10^{14}$ DT40 cells that contain different immunoglobulin heavy chain variable region genes.

Methods of Integrating or Diversifying Target Genes

According to certain embodiments of the present disclosure, there is provided a method for integrating a target gene into a chicken immunoglobulin heavy chain locus. Such a method comprises: (a) transfecting chicken B-cells with a recombinant polynucleotide vector for integrating a target gene into a chicken immunoglobulin gene heavy chain locus or a composition that comprises a plurality of such recombinant polynucleotide vectors as provided herein; and (b) identifying a chicken B-cell in which the target gene is integrated into the immunoglobulin heavy chain locus.

Step (a) may be performed using any methods known in the art for transfecting a chicken cell with a recombinant polynucleotide vector, including the method used in the Example below. Any chicken B-cells that allow for homologous recombination may be transfected. Additional description of such cells is provided above related to host cells.

Step (b) may be performed using any appropriate methods known in the art. For example, B-cells in which the target gene is integrated into the immunoglobulin heavy chain locus may be identified by Southern blot analysis using the target gene as a probe or by polymerase chain reaction (PCR) to amplify the nucleic acid fragment between the chicken immunoglobulin $V_H$ gene upstream nucleic acid sequence region and the chicken immunoglobulin $J_H$ gene downstream nucleic acid sequence region, followed by detecting the amplified nucleic acid fragment. In certain embodiments, the B-cells in which a target gene is to be integrated may already have a marker gene (e.g., the GFP gene) integrated into a chicken immunoglobulin gene heavy chain locus. The integration of the target gene into such B-cells may be identified by the replacement of the marker gene with the target gene, and hence the loss of the marker (e.g., fluorescence produced by GFP).

In another embodiment, the present disclosure provides a method for integrating a first target gene into a chicken immunoglobulin heavy chain locus and integrating a second target gene into a chicken immunoglobulin light chain locus. Such a method comprises (a) transfecting chicken B-cells with (1) a first recombinant polynucleotide vector for integrating a first target gene into a chicken immunoglobulin gene heavy chain locus or a first composition that comprises a plurality of such first recombinant polynucleotide vectors provided herein, and (2) a second recombinant polynucleotide vector for integrating a second target gene into a chicken immunoglobulin gene light chain locus or a second composition that comprises a plurality of such second recombinant polynucleotide vectors provided herein; and (b) identifying a chicken B-cell in which the first target gene is integrated into the immunoglobulin heavy chain locus and the second target gene is integrated into the immunoglobulin light chain locus.

Step (a) may be performed by first mixing one or more first recombinant polynucleotide vectors for integrating a first target gene into a chicken immunoglobulin gene heavy chain locus with one or more second recombinant vectors for integrating a second target gene into a chicken immunoglobulin gene light chain locus to form a mixture, and then transfecting chicken B-cells with such a mixture. Alternatively, chicken B-cells may be transfected separately with one or more first recombinant polynucleotide vectors and with one or more second recombinant polynucleotide vectors.

Step (b) may be performed using any appropriate methods known in the art. In certain preferred embodiments, B-cells into which first and second target genes are to be integrated may already have a first marker gene (e.g., the GFP gene) integrated into a chicken immunoglobulin gene heavy chain locus and a second marker gene (e.g., the BFP gene) integrated into a chicken immunoglobulin gene light chain locus. The integration of both the first and second target genes into such B-cells may be identified by the replacement of the first and second marker genes with the first and second target genes, thus the loss of both first and second markers (e.g., fluorescence produced by GFP and by BFP).

In another embodiment, the present disclosure provides a method for producing a repertoire (i.e., a library) of immunoglobulin heavy chain polypeptide sequence variants of a target polypeptide encoded by a target gene that comprises a rearranged immunoglobulin $V_H$-D-$J_H$ gene. Such a method comprises: culturing a B-cell containing a vector that comprises a rearranged immunoglobulin $V_H$-D-$J_H$ gene under conditions that allow for proliferation of the B-cell until a plurality of B-cells is obtained. The B-cell is capable of either or both of (i) somatic hypermutation in an immunoglobulin $V_H$ region-encoding sequence, which may include somatic hypermutation in an immunoglobulin $V_H$ complementartity determining region-encoding sequence and/or in an immunoglobulin $V_H$ framework region-encoding sequence, and (ii) gene conversion between a rearranged chicken immunoglobulin $V_H$-encoding nucleic acid sequence and a $V_H$ pseudogene nucleic acid sequence. The proliferation of the B-cell produces a repertoire of immunoglobulin heavy chain polypeptide sequence variants of the target polypeptide encoded by the target gene that comprises the rearranged immunoglobulin $V_H$-D-$J_H$ gene.

In certain embodiments, the target gene comprises a rearranged mammalian (e.g., human, mouse, or rabbit) or humanized immunoglobulin $V_H$-D-$J_H$ gene. In certain preferred embodiments, the target gene comprises a chicken rearranged immunoglobulin $V_H$-D-$J_H$ gene.

In certain embodiments, the B-cell to be proliferated may have been transfected with, and thus comprise a second vector for integrating a rearranged immunoglobulin $V_L$-$J_L$ gene into a chicken immunoglobulin gene light chain locus as disclosed herein. The rearranged immunoglobulin $V_L$-$J_L$ gene may be a rearranged mammalian (e.g., human, mouse, or rabbit) or humanized immunoglobulin $V_L$-$J_L$ gene. In preferred embodiments, the rearranged immunoglobulin $V_L$-$J_L$ gene is a rearranged chicken immunoglobulin $V_L$-$J_L$ gene.

In certain embodiments, the B-cell to be proliferated may comprise a polymerized lactose operator in its immunoglobulin gene heavy or light chain locus. As described above, the polymerized lactose operator facilitates diversification of target gene(s).

In another aspect, the present disclosure provides a method for screening B-cells for the production of antibodies that specifically bind to a given antigen. As described above, chicken B-cells (e.g., DT40 cells) may be transfected with a first recombinant polynucleotide vector that comprises a rearranged immunoglobulin $V_H$-D-$J_H$ gene and a second recombinant polynucleotide vector that comprises a rearranged immunoglobulin $V_L$-$J_L$ gene to obtain a chicken B-cell having the rearranged immunoglobulin $V_H$-D-$J_H$ gene integrated into its immunoglobulin gene heavy chain locus and the rearranged immunoglobulin $V_L$-$J_L$ gene integrated into its immunoglobulin gene light chain locus. Such chicken B-cells may be further cultured to obtain a plurality of B-cells that produce a repertoire of immunoglobulin heavy chain polypeptide sequence variants as well as a repertoire of immunoglobulin light chain polypeptide sequence variants. The plurality of B-cells may be screened for their production of antibodies that bind to a specific antigen.

Any methods appropriate for screening B-cells for their production of antigen-specific antibodies known in the art may be used. For example, binding of immunoglobulin molecules to specific antigens can be detected as interaction with fluorescent derivatives of the antigens analyzed by flow immunocytofluorimetry; and B-cells that bind to a specific antigen can be recovered upon sorting by the same or a similar flow cytometry technique (e.g., fluorescence activated cell sorting, FACS). B cells that bind to specific antigens can also be selected on solid supports carrying those antigens, for example, antigen-coated magnetic beads. Conversely, binding to solid supports may also permit removal of B-cells with unwanted binding specificities in an appropriately configured technique, such as depletion of cells by "panning" on antigen-coated plates. Exemplary methods for screening B-cells for producing antibodies specific to particular antigens include magnetic-activated cell sorting (MACS) and fluorescence-activated cell sorting (FACS) as described in the Example. Multiple rounds of selection may be performed to identify B-cells with sufficient binding affinity to the specific antigen.

In certain embodiments, the rearranged immunoglobulin $V_H$-D-$J_H$ gene and the rearranged immunoglobulin $V_L$-$J_L$ gene integrated into chicken immunoglobulin gene heavy and light chain loci, respectively, are a human rearranged immunoglobulin $V_H$-D-$J_H$ heavy chain gene and a human rearranged immunoglobulin $V_L$-$J_L$ light chain gene. The method for screening B-cells for producing antibodies specific for a particular antigen described above is thus able to directly identify B-cells that produce human antibodies that bind to the antigen. Such B-cells may already have had chicken heavy and light chain constant region genes replaced by human heavy and light chain constant region genes, before integration of human rearranged immunoglobulin $V_H$-D-$J_H$ and $V_L$-$J_L$ genes into chicken immunoglobulin gene heavy and light chain loci.

In certain embodiments, the rearranged immunoglobulin $V_H$-D-$J_H$ gene and the rearranged immunoglobulin $V_L$-$J_L$ gene integrated into chicken immunoglobulin gene heavy and light chain loci, respectively, are a humanized rearranged immunoglobulin $V_H$-D-$J_H$ gene (e.g., those containing human heavy chain framework regions) and a humanized rearranged immunoglobulin $V_L$-$J_L$ gene (e.g., those containing human light chain framework regions). The method for screening B-cells for producing antibodies specific for a particular antigen described above is thus able to directly identify B-cells that produce humanized antibodies that bind to the antigen.

In certain embodiments, the rearranged immunoglobulin $V_H$-D-$J_H$ gene and the rearranged immunoglobulin $V_L$-$J_L$ gene integrated into chicken immunoglobulin gene heavy and light chain loci, respectively, are a chicken rearranged immunoglobulin $V_H$-D-$J_H$ gene and a chicken rearranged immunoglobulin $V_L$-$J_L$ gene. In preferred embodiments, the rearranged immunoglobulin $V_H$-D-$J_H$ gene and the rearranged immunoglobulin $V_L$-$J_L$ gene are obtained from a population of chicken bursa of Fabricius cells. The method for screening B-cells for producing antibodies specific for a particular antigen described herein is thus able to identify B-cells that produce chicken antibodies that bind to the antigen. The obtained chicken antibodies may be further humanized using methods described herein and known in the art.

The antibodies obtained by the above-described methods may have diagnostic and therapeutic applications. In addition, the methods are adaptable to high throughput approaches, and may be especially suitable for developments of monoclonal antibodies for personalized medicine.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references in microbiology, molecular biology, biochemistry, molecular genetics, cell biology, virology and immunology techniques that are cited and discussed throughout the present specification. See, e.g., Sambrook, et al., *Molecular Cloning: A Laboratory Manual*, 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, N.Y.); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and CC Blackwell, eds., 1986); Riott, *Essential Immunology*, 6th Edition, (Blackwell Scientific Publications, Oxford, 1988); *Embryonic Stem Cells: Methods and Protocols (Methods in Molecular Biology)* (Kurstad Turksen, Ed., 2002); *Embryonic Stem Cell Protocols: Volume I: Isolation and Characterization (Methods in Molecular Biology)* (Kurstad Turksen, Ed., 2006); *Embryonic Stem Cell Protocols: Volume II: Differentiation Models (Methods in Molecular Biology)* (Kurstad Turksen, Ed., 2006); *Human Embryonic Stem Cell Protocols (Methods in Molecular Biology)* (Kursad Turksen Ed., 2006); *Mesenchymal Stem Cells: Methods and Protocols (Methods in Molecular Biology)* (Darwin J. Prockop, Donald G. Phinney, and Bruce A. Bunnell Eds., 2008); *Hematopoietic Stem Cell Protocols (Methods in Molecular Medicine)* (Christopher A. Klug, and Craig T. Jordan Eds., 2001); *Hematopoietic Stem Cell Protocols (Methods in Molecular Biology)* (Kevin D. Bunting Ed., 2008) *Neural Stem Cells: Methods and Protocols (Methods in Molecular Biology)* (Leslie P. Weiner Ed., 2008).

Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers. By "consisting of" is meant including, and typically limited to, whatever follows the phrase "consisting of:" By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and may or may not be present depending upon whether or not they affect the activity or action of the listed elements.

In this specification and the appended claims, the singular forms "a," "an" and "the" include plural references unless the content clearly dictates otherwise. As used herein, in particular embodiments, the terms "about" or "approximately" when preceding a numerical value indicates the value plus or minus a range of 5%, 6%, 7%, 8% or 9%. In other embodiments, the terms "about" or "approximately" when preceding a numerical value indicates the value plus or minus a range of 10%, 11%, 12%, 13% or 14%. In yet other embodiments, the terms "about" or "approximately" when preceding a numerical value indicates the value plus or minus a range of 15%, 16%, 17%, 18%, 19% or 20%.

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The following example is for illustration and is not limiting.

EXAMPLE

The following materials and methods were used in this example:

Cell Culture and Gene Targeting.

DT40-derived cell lines (Cummings et al., 2007; Cummings et al., 2008; Yabuki et al., 2009;} and as described herein) were maintained and transfected as previously described (Yabuki et al., 2005). FreeStyle 293-F cells (Invitrogen, Carlsbad, Calif.) were maintained and transfected as specified by the manufacturer.

PolyLacO was targeted to the $\psi V_H$ array at the rearranged and expressed heavy chain allele of DT40 PolyLacO-$\lambda_R$ cells, previously engineered to carry the PolyLacO at the rearranged and expressed light chain allele (Cummings et al., 2007; Cummings et al., 2008; Yabuki et al., 2009). The PolyLacO regulatory element {Robinett et al., 1996) comprised approximately 100 repeats of a 20-mer lactose operator (LacO). The targeting construct, pPolyLacO-$\psi V_H$, carried the blasticidin-resistance gene to enable selection of stable transfectants following about 10 days growth in 20 µg/ml concentration of blasticidin (Invitrogen). To generate this construct, 2.8- and 4.2-kb homology arms were obtained from the $\psi V_H$ array fragments amplified from DT40 genomic DNA using primers 5'-GGGGTCTC-TATGGGGTCTAAGCGTGGCC-3' (SEQ ID NO:1) and 5'-GGCCGATTCTTTTCTCATGAGATCCCTCCAGAAG-3' (SEQ ID NO:2) or 5'-TTCCCCACAACCAGGCCAT-GCGCCTCCTTG-3' (SEQ ID NO:3) and 5'-CCTGCAGA-CACCCAGAGGAGGGCTCAGC-3' (SEQ ID NO:4). The PolyLacO, the blasticidin-resistance gene, and two homology arms were subcloned into pBluescript II KS(+) (Stratagene). The construct was verified by restriction analyses and partial sequencing, and propagated in recombination-deficient E. coli strains Stbl2 (Invitrogen) to maintain repeat stability. Targeting was carried out essentially as previously described (Yabuki et al., 2009). DT40 PolyLacO-$\lambda_R$ cells were transfected, and following 10 days culture in the presence of antibiotic, stable transfectants were screened by genomic PCR and Southern blotting to identify homologous integrants.

The $V_H$ (VDJ) region repertoire of DTLacO cells was enhanced in two steps, both of which relied on the targeting vector, pVDJ3. To generate pVDJ3, 22- and 1.8-kb homology arms were amplified from DT40 genomic DNA using primers 5'-TGAATGCTTTGTTAGCCCTAATTAGGGAT-TGAATTGAGAG-3' (SEQ ID NO:5) and 5-CCGT-GAGACCCCCCGTTGACC-3' (SEQ ID NO:6) or 5'-GC-CCGACCGAAGTCATCGTCTCCTCCGGTG-3'(SEQ ID NO:7) and 5'-TTTGCCTTCAAATCACCCTA-3' (SEQ ID NO:8), respectively, and fused to the leader-VDJ region and cloned into pBluescript II KS(+). The pVDJ3-GFP targeting construct derivative was generated by replacing the leader-VDJ region with a GFP expression cassette (McConnell Smith et al., 2009). The pVDJ3-Bin1 targeting construct pool was generated by inserting a library of $V_H$ region into the XcmI-PshAI site of pVDJ3. Those sequences had been amplified from the bursa of a 2 month-old White Leghorn chick using PCR primers 5'-GGGTCTGCGGGCTC-TATGGGG-3' (SEQ ID NO:9) and 5'-ATCGCCGCG-GCAATTTTGGGG-3' (SEC) ID NO:10). In the first step, the endogenous VDJ region was replaced by the GFP expression cassette using pVDJ3-GFP. In the second step, the pVDJ3-Bin1 targeting construct pool was used to replace the previously targeted GFP, producing sIgM$^+$ cells. Transfections for heavy chain targeting were carried out using a NUCLEOFECTOR™ (program B-023; Lonza).

sIgM$^+$ cells were collected by MACS and then FACS. Briefly, following two days posttransfection, cells were washed in PBS containing 1% BSA (Sigma, St. Louis, Mo.), and sigM$^+$ cells enriched by binding to protein G DYNA-BEADS® (Dynal) coupled to anti-chicken IgM (Southern Biotech) according to manufacturers' directions. After three days in culture, sIgM$^+$/GFP$^-$ cells were sorted using a FACSARIA™ (BD Biosciences), generating the DTLacO-2 population.

VJ Targeting Constructs.

To target new VJ sequences, pVJ1 was constructed. A 3.2-kb fragment of the VJ upstream region was amplified with PCR primers 21-22 (5'-GGGACACCTGAAGGCAT-GAGTGG-3', SEQ ID NO:21) and (5'-GGCGGAATCCCA-GCAGCTGTGT-3', SEQ ID NO:22); a 1.2-kb fragment of the VJ downstream region was amplified with PCR primers 23-24 (5'-GTGAGTCGCTGACCTCGTCTCGGTC-3', SEQ ID NO:23) and (5'-GGGCTCTTTCTACCT-CAAGGCATGT-3', SEQ ID NO:24); and both fragments were cloned into pCR2.1 (Invitrogen). The leader-VJ region was then inserted into the BmgBI-AvrII site of the plasmid. The construct was verified by restriction analyses and sequencing. New VJ sequences were also ligated into the BmgBI-AvrII site.

To target BFP to the DT40 VJ region, pVJ1-BFP was made. BFP and SV40 poly A signal sequences were amplified from pTagBFP-N (Evrogen); a 155-bp of the VJ upstream region was fused to the amplicon; and then inserted into the BmgBI-AvrII site of the VJ vector.

To add FLAG-tag to the VJ, pVJ1-FLAGA was made. A short FLAG-tag (DYKDE, SEQ ID NO:25) was inserted just upstream of the mature VJ region by site-directed mutagenesis.

C-Region Targeting Constructs.

An expression construct of chicken-human chimeric heavy-chain was first generated: chVDJ-huCγ1-FLAG-TEV-chTMD, and it was confirmed that this fusion polypeptide was paired with chicken λ light-chain and expressed on the surface of DT40 cells.

To generate the C-region replacing construct, a 4-kb fragment of the Cµ1 upstream region was amplified from DT40 genomic DNA with XP0090 (5'-AGCCTCATTATC-CCCCTGAT-3', SEQ ID NO:26; designed based on GenBank No. AB029075.1) and XP0094 (5'-TCTCTTTCCCT-TCGCTTTGA-3', SEQ ID NO:27) and a 6-kb fragment of the Cµ1-Cµ2 region was amplified with XP0095 (5'-ACA- GTTCCGTTCCGGTATG-3', SEQ ID NO:28) and XP0099 (5'-CACTCCATCCTCTTGCTGGT-3', SEQ ID NO:29). The upstream was cloned into the EcoRV site of the pBluescript II KS(+) (Stratagene); huCγ1-FLAG-TEV-chTMD and BGH poly A signal sequences were fused to just downstream of the inserted upstream sequence by QUIKCHANGE™ site-directed mutagenesis (Stratagene); and then the downstream was cloned into the HindIII-XhoI site of the plasmid. Zeocin marker flanked by modified loxP sites was also inserted into the HindIII site to provide a drug selection mechanism for stable transfectants, if needed subsequently. The construct was verified by restriction analyses and partial sequencing, and propagated in recombination-deficient E. coli strains Stbl2 or Stbl3 (Invitrogen) to maintain S-region repeat sequences.

To prevent possible B cell receptor (BCR)-induced apoptosis due to binding of membrane-anchored IgM to target antigens with high-affinity, a mutant version of the C-region replacing construct was made. Two amino acids Ser-Thr within the transmembrane domain (TMD), which are crucial for signal transduction (Shaw, A. C., Mitchell, R. N., Weaver, Y. K., Campos-Torres, J., Abbas, A. K. & Leder, P. Cell 63, 381-392 (1990)), were substituted to Val-Val by site-directed mutagenesis.

Both wild-type and mutant targeting constructs were also designed to have protease cleavage sites in case it became desirable for chimeric antibodies to be released from cells. One was full-length FLAG-tag (DYKDDDDK, SEQ ID NO:30; which could be cleaved by enterokinase) and the other was TEV recognition site (ENLYFQG, SEQ ID NO:31; which could be cleaved by TEV protease).

To replace heavy-chain C-region, wild-type DT40 cells were transfected with either C-region replacing construct using a NUCLEOFECTOR™ (Lonza); and after 3 days posttransfection, chicken-human chimeric antibody-expressing cells were enriched by MACS with DYNABEADS® Protein G (Invitrogen). The expression of the fusion protein was detected by FACS with anti-human IgG (Southern Biotech) and the sequences of the expressed chVDJ-huCγ1-FLAG-TEV-chTMD fusions were confirmed by RT-PCR.

The nucleotide sequence encoding chVDJ-huCγ1-FLAG-TEV-chTMD is set forth in SEQ ID NO:32, in which the component nucleotide sequences encoding the chVDJ, huCγ1, FLAG, TEV, and chTMD fragments are set forth in SEQ ID NOS:33-37, respectively.

Quantitation of Diversification Rates.

Diversification rates were quantified using the sIgM loss assay, which measured the fraction of cells that have lost expression of IgM on the cell surface due to diversification events (Sale et al., 2001; Yabuki et al., 2005; Ordinario et al., 2009). In brief, panels of approximately 20 independent transfectants were expanded for 3 weeks, then cells (~1× $10^6$) from each panel member were stained with R-PE conjugated anti-chicken IgM (1:200; Southern Biotech), and analyzed on a FACScan with CellQuest software (BD Biosciences). The percentage of sIgM⁻ cells was calculated as the ratio of the number of cells with 8-fold or greater decrease in PE intensity to the PE of the sIgM⁺ population (Hatanaka et al., 2005; Sale et al., 2001).

V Region Sequence Analysis.

V-region PCR and sequence analysis were performed essentially as described (Yabuki et al., 2005; Cummings et al., 2007), using primers 5'-CAGGAGCTCGCGGGGC-CGTCACTGATTGCCG-3' (SEQ ID NO:11) and 5-GCG-CAAGCTTCCCCAGCCTGCCGCCAAGTCCAAG-3' (SEQ ID NO:12) for amplification of the rearranged $V_\lambda$ regions and primers 5'-GGGTCTGCGGGCTCTATGGGG-3' (SEQ ID NO:13) and 5'-ATCGCCGCG-GCAATTTTGGGG-3' (SEQ ID NO:14) for amplification of the rearranged $V_H$ regions When necessary, semi-nested PCR was carried out using a second-round primer 5'-TCACTGATTGCCGTTTTCTCCCCTCTCTCC-3' (SEQ ID NO:15) for the $V_\lambda$ regions or 5'-GGT-CAACGGGGGGTCTCACGG-3' (SEQ ID NO:16) for the $V_H$ regions. PCR products were purified with QIAQUICK™ PCR purification kit (Qiagen, Valencia, Calif.) and sequenced directly.

Antigens and Selection for Antigen Binding.

Initial selections were performed by binding diversified DTLacO populations to magnetic beads complexed with antigens, and subsequent selections by FACS using fluorescence-labeled soluble antigens, following procedures previously described (Cumbers et al., 2002; Seo et al., 2005) with minor modifications. SAv DYNABEADS® M-280 (Dynal) and SAv-PE (Southern Biotech) were used to select cells that recognized SAv. Selection of cells that recognized human cell surface proteins used recombinant human chimeric proteins, expressed as fusions with human IgG1 Fc (R&D Systems, Minneapolis, Minn.), including the extracellular domain of VEGFR2 (residues 20-764; Cat. no. 357-KD), TIE2 (residues 23-745; Cat. no. 313-TI), TROP2 (residues 88-274; Cat. no. 650-T2), FN14 (residues 28-79; Cat. no. 1199-TW) or FZD10 (residues 21-161; Cat. no. 3459-FZ). Chimeric proteins were bound to protein G DYNA-BEADS® (Dynal) using manufacturers' recommended conditions for the MACS method, and detected with PE-Cy5-labeled anti-human IgG Fc (Southern Biotech; 1:200) for the FACS method. Chimeric proteins were bound to protein G DYNABEADS® (Dynal) using the manufacturers' recommended conditions for the MACS method, and detected with PE-Cy5-labeled anti-human IgG Fc (Southern Biotech; 1:200) for the FACS method. Antigens for selection were used at concentrations of 10 μg/ml; selections were carried out on >$10^8$ cells at a bead:cell ratio ranging from 3:1 to 1:1. In some cases, pre-clearing of non-specific DTLacO cells was carried out using beads lacking antigen.

Binding and Affinity Assays.

Saturation binding kinetics were determined by staining cells with various concentrations of fluorescent-labeled soluble antigens, and apparent affinities ($k_D$) were calculated by nonlinear regression using GRAPHPAD™ Prism software. To test binding of mAbs to the cell surface antigens, recombinant chimeric chicken-human mAbs were generated by cloning PCR-amplified $V_H$ and $V_\lambda$ segments in frame into pcDNA3.1 (Invitrogen) derivatives, pcDNA3.HG1 and pcDNA3.HLam, carrying the human γ1 and λ constant regions, respectively. The expression plasmids were cotransfected transiently into FREESTYLE™ 293-F cells (Invitrogen, Carlsbad, Calif.) according to the manufacturer's instructions. After 2-4 days culture, secreted antibodies were purified from supernatants by protein A chromatography (MabSelect SuRe; GE Healthcare) and, if necessary, concentrated by ULTRACEL™ ultrafiltration (Millipore). Target cells were generated by transient transfection of 293-F cells with antigen expression constructs (GeneCopoeia).

The following results were obtained:

The DTLacO mAb Discovery Platform.

The DTLacO platform for rapid mAb selection and optimization was engineered in two steps (FIG. 1). First, a potent regulatory element, multimers of the lactose operator DNA from the E. coli lactose operon ("PolyLacO"), was inserted upstream of the rearranged and expressed IgH gene in the DT40 PolyLacO-$\lambda_R$ cell line, previously engineered to carry PolyLacO at Igλ only. Next, the endogenous $V_H$ (VDJ) region was substituted with a $V_H$ library generated from chicken bursal B cells, expanding the initial $V_H$ repertoire. Both steps of engineering took advantage of the high efficiency of gene targeting in chicken DT40 B cells.

It was previously demonstrated that PolyLacO can enable inducible regulation of the rate and outcome of Igλ gene diversification (somatic hypermutation or gene conversion) upon expression of distinct regulatory factors fused to lactose repressor protein (LacI) (Cummings et al., 2007; Cummings et al., 2008; Yabuki et al., 2009). This use of the LacO/LacI regulatory network took advantage of the high-affinity ($k_D=10^{-14}$ M) of LacI for LacO, as well as the sensitivity of the LacI/LacO interaction to the small molecule, IPTG.

Synergistic Acceleration of Diversification by PolyLacO Targeted to both Igλ and IgH.

Figure 2A:
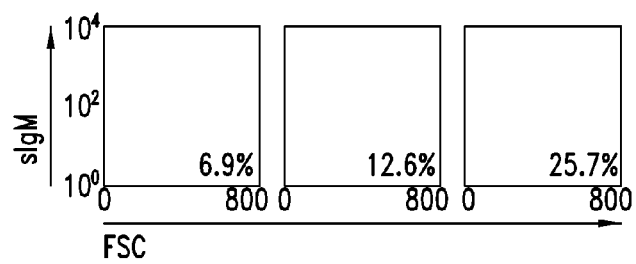
FIGS. 2A-2C show accelerated clonal diversification rate in DTLacO cells. (A) Surface IgM (sIgM) loss assay of three representative clonal DTLacO LacI-HP1 transfectants. Fraction of sIgM⁻ cells in each culture is indicated at lower right in each panel. (B) Summary of sIgM loss assays. Each open circle represents the percentage of sIgM⁻ cells in one clonal transfectant, analyzed three weeks post-transfection. Cells analyzed were: DT40 PolyLacO-$\lambda_R$ GFP-LacI control transfectants (n=27); DT40 PolyLacO-$\lambda_R$ LacI-HP1 transfectants (n=16), and DTLacO LacI-HP1 transfectants (n=20). (C) Median sIgM loss of DT40 PolyLacO-$\lambda_R$ LacI-HP1 and DTLacO LacI-HP1 transfectants relative to GFP-LacI control transfectants.
Figure 2B:
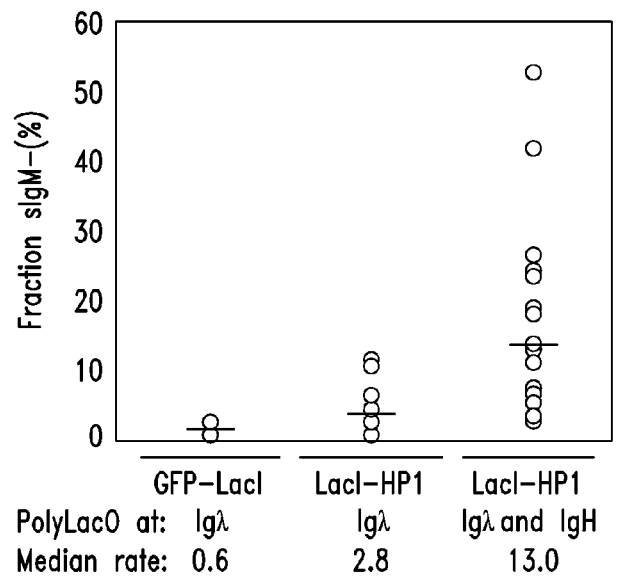
Figure 2C:
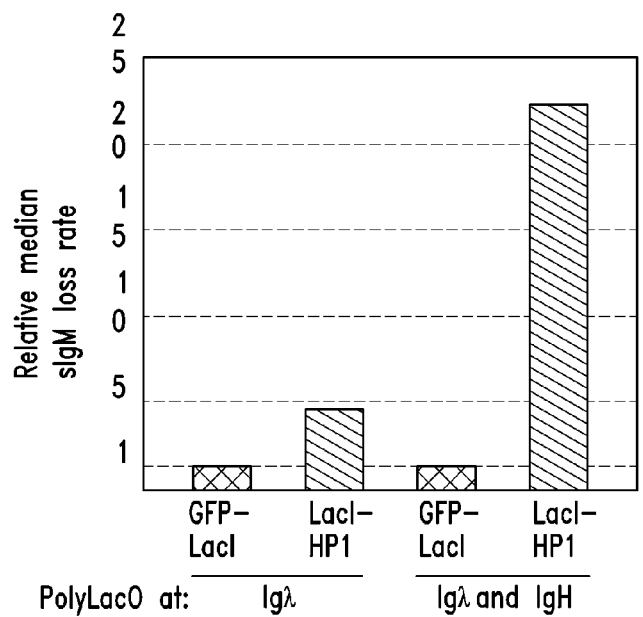

Diversification was predicted to be elevated in "DTLacO" cells, engineered to carry PolyLacO targeted to both the IgA and the IgH genes, relative to DT40 PolyLacO-$\lambda_R$ cells, which carried PolyLacO only at IgA. Diversification rates of candidate engineered lines were determined by assaying the fraction of sIgM⁻ cells 3 weeks post-transfection with the LacI-HP1 regulatory factor. Representative candidates exhibited diversification rates of 6.9%, 12.6% and 25.7% (e.g., FIG. 2A), from 2.5- to 9.2-fold elevated relative to the 2.8% characteristic of the parental DT40 PolyLacO-$\lambda_R$ LacI-HP1 line. Accelerated diversification was reconfirmed for one line by fluctuation assay of individual transfectants (FIG. 2B). Percentages of sIgM⁻ cells ranged from 2.5% to 52.5%, with a median of 13.0% (FIG. 2B), 4.6-fold higher than in DT40 PolyLacO-$\lambda_R$ LacI-HP1 transfectants (2.8%), and 21.7-fold higher than in control DT40 PolyLacO-$\lambda_R$ GFP-LacI cells (0.6%, comparable to the DT40 parental line (Cummings et al., 2007). Some individual clones exhibited sIgM loss considerably different than the median, as predicted because this fluctuation assay measured accumulated sIgM⁻ variants. Thus, targeting PolyLacO elements to both the heavy and light chain genes accelerated diversification nearly 22-fold relative to the DT40 parental cell line (FIG. 2C). Diversification was also accelerated upon transfection of other factors, including LacI-VP16 and E47-LacI (not shown).

Ex Vivo Evolution of Anti-Streptavidin Antibodies.

To test the utility of DTLacO cells for ex vivo mAb evolution, mAbs against the model antigen, streptavidin (SAv) (Cumbers et al., 2002; Seo et al., 2005) were selected from the DTLacO-1 population (FIG. 1, Step 1). Cells were stably transfected with an E47-LacI expression construct, which encoded a fusion of LacI and the E47 isoform of the regulatory factor, E2A. E47 was a known transcriptional regulator in some contexts, but at the Ig genes of DT40 cells it promoted diversification but not transcription (Yabuki et al., 2009). A diversified population of 3×10⁸ DTLacO E47-LacI cells was enriched twice for binding to SAv-conjugated magnetic beads, and then selected by successive rounds of FACS for binding to SAv-PE. The cell population exhibited increased affinity after each round of selection. A 30-fold shift was evident after the fifth round of selection and a 100-fold shift by the seventh round (S5 and S7, respectively; FIG. 3A). The binding affinity of the S7 population for SAv-PE-Cy7 was measured by saturation binding kinetics. In this FACS-based method, cells were stained with increasing concentrations of antigen until equilibrium of bound and unbound antigen was established; the resulting mean fluorescence intensity (MFI) values were analyzed with Prism software (GraphPad); and the affinity at equilibrium ($k_D$) was determined (FIG. 3B). The apparent affinity was found to be 0.7 nM, after 7 rounds of selection, which compared favorably with 15-19 rounds of selection that were required for selection of antibodies of comparable affinity ex vivo using cultured human B cell lines (Cumbers et al., 2002). The sequences of the $V_H$ and $V_\lambda$ regions were determined by PCR amplification from single cells, and compared to the germline (Reynaud et al., 1987; Reynaud et al., 1989). Strikingly, an 18 residue insertion/duplication was identified in CDR1 of $V_\lambda$ (FIG. 3C). An insertion in light chain CDR1 of anti-SAv mAbs has also been reported by others using DT40 cells that have not undergone any genetic engineering (Seo et al., 2005).

Selection of High Affinity mAbs that Recognize Conserved Cell Surface Receptors.

Figure 4A:
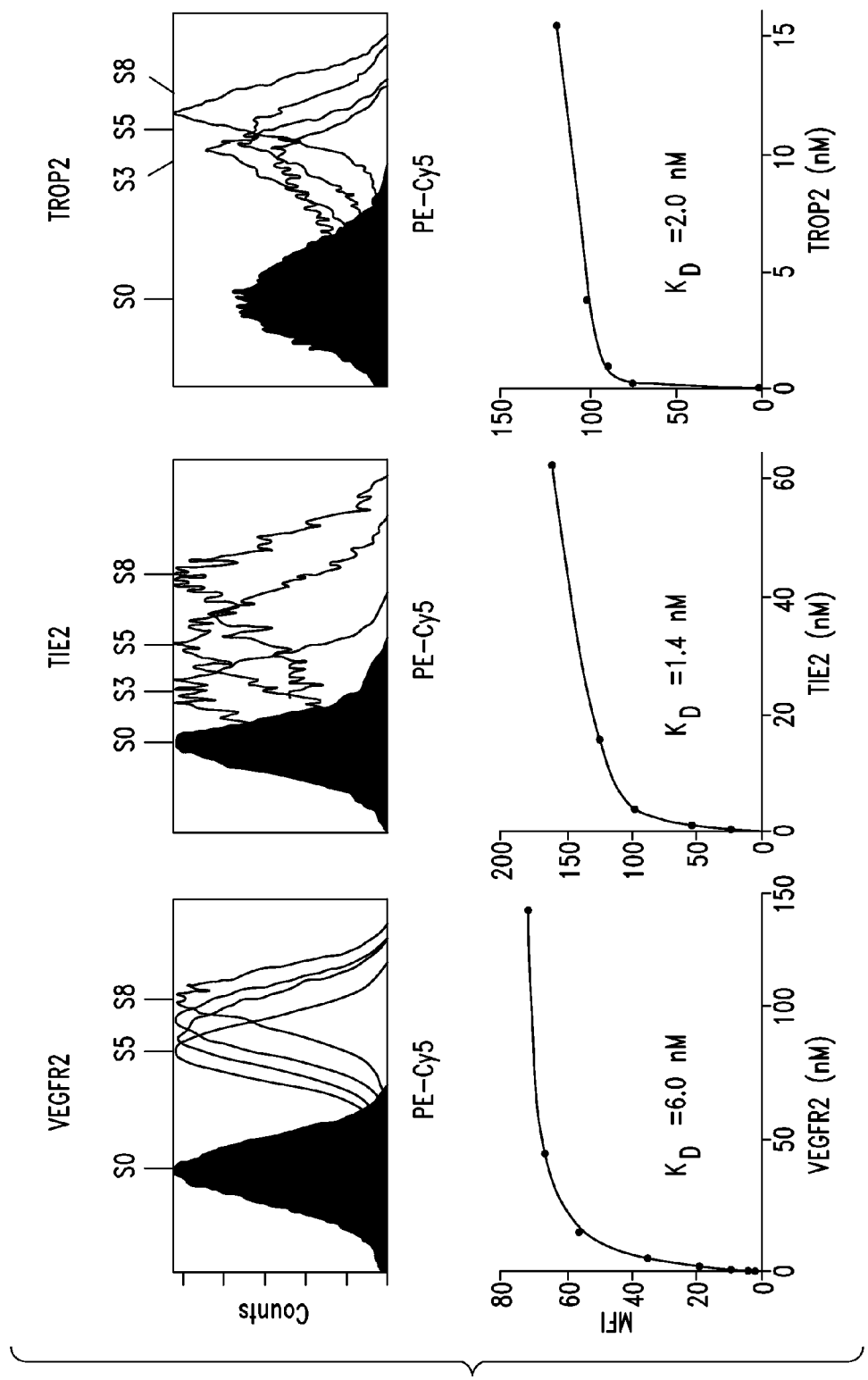
FIGS. 4A-4C show high affinity mAbs selected from DTLacO cells. (A) Above, binding profiles of successive DTLacO LacI-HP1 populations selected for recognition of cell surface receptors, VEGFR2, TIE2 and TROP2. Rounds of selection designated above peaks (S0-S8). Below, saturation binding kinetics, indicating apparent $k_D$. (B) Specificity of selected DTLacO populations. FACS analysis of binding of cell populations selected for high affinity recognition of VEGFR2, TIE2 or TROP2 to recombinant VEGFR2, TIE2, TROP2, SAv or ovalbumin (OVA). Solid peaks represent the negative reference control (secondary antibody alone), and heavy solid lines represent staining for the indicated antigen. (C) Schematic alignment of $V_H$ and $V_\lambda$ regions of mAbs selected for binding to VEGFR2, TIE2 and TROP2. Light horizontal lines represent chicken framework regions, heavy horizontal lines enclosed in boxes identify CDRs, vertical bars indicate single residue differences relative to the most common DTLacO sequence, and triangle indicates insertion.
Figure 4B:
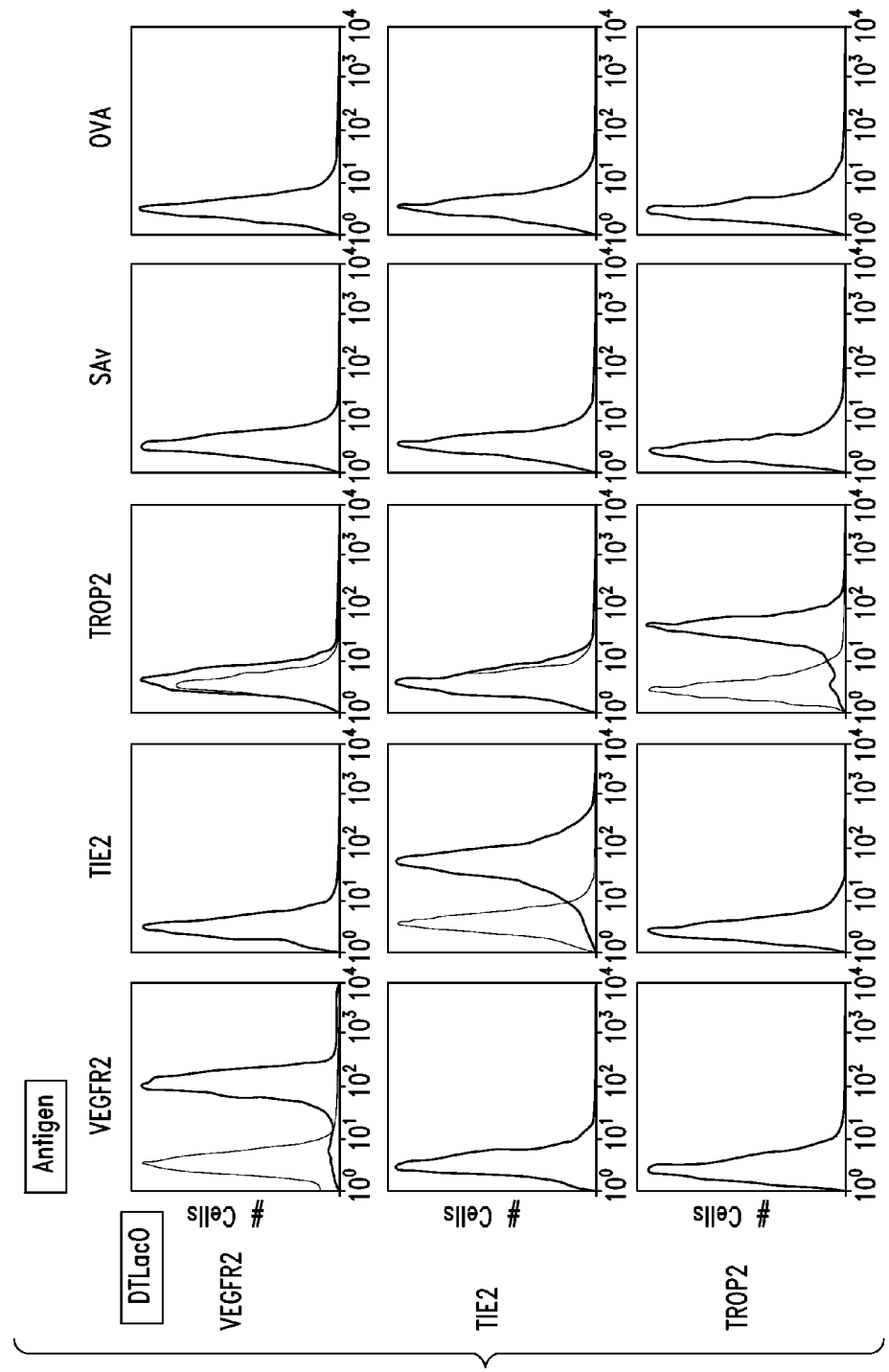

The DTLacO-1 cells stably expressing LacI-HP1 were selected to identify mAbs against three cell surface antigens of therapeutic interest: the receptor tyrosine kinases, VEGFR2 and TIE2, which play essential roles in physiologic and pathologic angiogenesis, most notably in cancer (Huang et al., 2010; Ferrara et al., 2010); and the glycoprotein, TROP2, which is overexpressed in numerous epithelial cancers (Cubas et al., 2010). The extracellular domains of these receptors were highly conserved, with the human and murine orthologs exhibiting 80%, 90%, and 83% identity, respectively. Each extracellular domain was expressed as recombinant protein fused to the human IgG1 Fc domain. DTLacO cells specific for each antigen were enriched from 1×10⁹ cells by initial selection on the antigen bound to magnetic beads, and then by binding to the soluble antigen and sorting via FACS. Eight successive selected populations were characterized and shown to exhibit increased affinity at each selection step (FIG. 4A, above). At the eighth selection step, analysis of saturation binding kinetics of the soluble antigens VEGFR2, TIE2, and TROP2 to their cognate DTLacO populations established apparent affinity values ($k_D$) of 6.0, 1.4, and 2.0 nM, respectively (FIG. 4A, below). Specificity of individual selected populations was tested by assaying binding to a panel of antigens (VEGFR2, TIE2, TROP2, SAv and ovalbumin). The selected DTLacO cells recognized only the cognate target, and were not cross-reactive (FIG. 4B).

CDR-Targeted Mutations Characterized High Affinity mAbs.

Figure 4C:
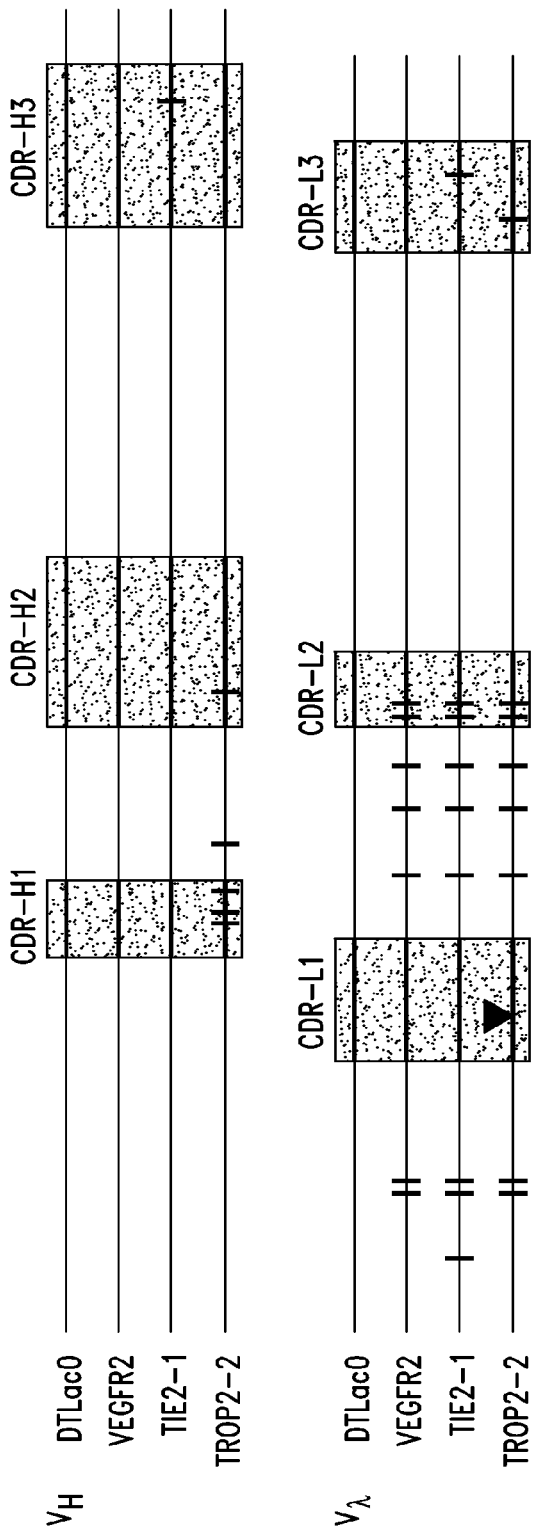

Recombinant, chimeric chicken-human mAbs were generated by cloning the $V_H$ and $V_\lambda$ regions from the DTLacO cells that recognized VEGFR2, TIE2 or TROP2 into a construct for expression fused to human γ1 heavy- and λ light-chain constant regions. The chimeric mAbs preserved high affinity antigen recognition (data not shown), showing that the B cell receptor conferred high affinity binding by the selected cells. Sequence analysis of the cloned $V_H$ and $V_\lambda$ regions showed that mutations conferring high affinity and specificity mapped primarily to CDRs (FIG. 4C). Both templated and nontemplated mutations were evident in the CDRs.

Expanded $V_H$ Diversity Further Accelerated mAb Selection.

Figure 5A:
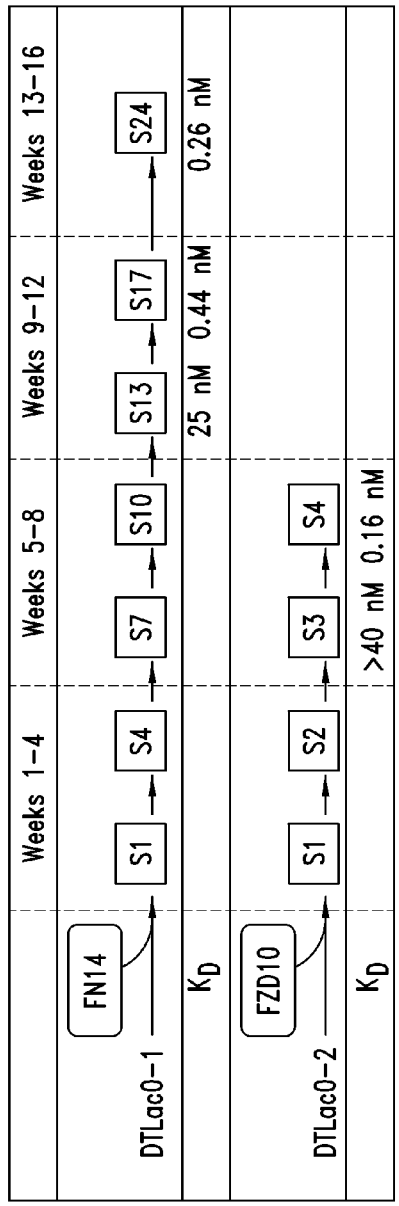
FIGS. 5A-5D show selection and humanization of anti-FN14 and anti-FZD10 mAbs. (A) Schematic of time course of selection of anti-FN14 and anti-FZD10 mAbs, with selection steps indicated by S, and apparent affinities ($k_D$) of recombinant chimeric mAbs shown below. (B) Schematic alignment of $V_H$ and $V_\lambda$ regions of mAbs selected for binding to FN14 and FZD10. Light horizontal lines represent chicken framework regions, heavy horizontal lines enclosed in boxes identify CDRs, vertical bars indicate single residue differences relative to the most common DTLacO sequence, and triangle indicates insertion. (C) Antibody humanization. $V_H$ and $V_\lambda$ regions of humanized mAbs hFS24 and hFZ2 schematically aligned to the human $V_H$-III or $V_\lambda$-III consensus (top lines). Light horizontal lines represent human framework regions; asterisks denote the two residues eliminated from the N-terminal of the light chain; vertical lines outside boxes identify Vernier zone residues preserved in humanized mAbs; other notations as in Panel B. (D) Apparent affinities ($k_D$) of humanized and progenitor FZ2 (anti-FZD10) mAbs.

DTLacO cells expressing regulatory LacI-fusion factors, from either the initial population (DTLacO-1) or the population engineered by $V_H$ replacement as described herein (DTLacO-2) (FIG. 1), were the sources of mAbs recognizing two other antigens of therapeutic interest, the small TNF receptor family member, FN14 (Winkles et al., 2008), and the G protein-coupled receptor, FZD10 {Katoh et al., 2007). Both proteins had highly conserved extracellular domains (92% and 94% identity, respectively, between human and mouse). As described in U.S. application Ser. No. 13/416, 752 and PCT/US2012/28584, an anti-FN14 mAb (FS24) was selected from the DTLacO-1 population and matured by LacI-HP1-driven diversification (FIG. 5A). Subnanomolar affinity ($k_D$=0.44 nM) was achieved after 17 rounds of selection over 12 weeks, and affinity improved modestly in the course of 7 additional selections over the next 4 weeks ($k_D$=0.26 nM).

Figure 5B:
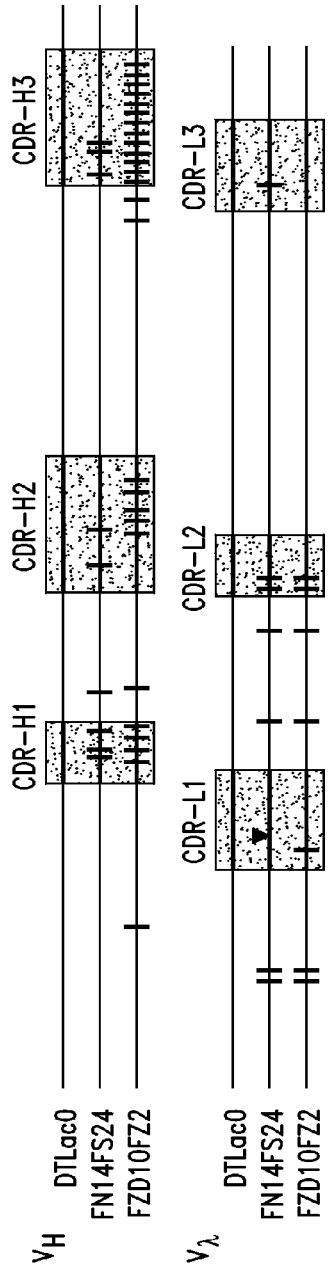

An anti-FZD10 mAb (FZ2)(U.S. application Ser. No. 61/523,102) was selected from the DTLacO-2 population described herein, with diversification accelerated by the tethered factor HIRA-LacI (Cummings et al., 2008). The population reached subnanomolar affinity after only four rounds of selection, over 8 weeks (FIG. 5A). This mAb recognized its target with apparent affinity $k_D$=0.16 nM. Sequence analysis of the cloned $V_H$ and $V_\lambda$ regions showed that mutations conferring high affinity and specificity mapped primarily to CDRs (FIG. 5B.)

Facile Humanization of Chicken Antibodies.

Figures 5C, 5D:
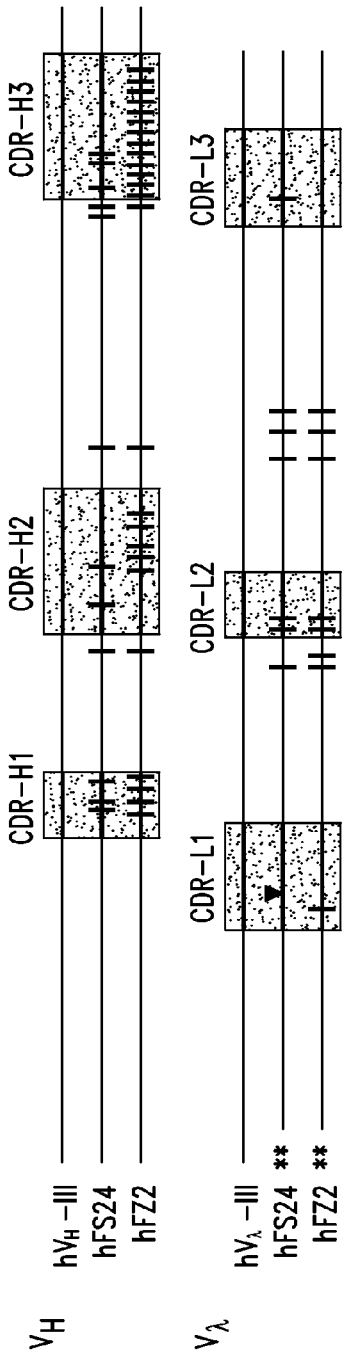

Antibodies selected in mice or other species are typically humanized for therapeutic applications (Almagro et al., 2008). The anti-FZD10 mAb was chosen for humanization, as its high affinity and distinct heavy-chain CDRs offered a robust test of this key step in mAb development. Chicken $V_H$ and $V_\lambda$ regions were most closely related to human $V_H$ subgroup III and $V_\lambda$ subgroup III, respectively. These were well-established frameworks for humanization, and have been used previously to humanize mAbs elicited by immunization of chickens (Tsurushita et al., 2004; Nishibori et al., 2006). The structure of a CDR is determined not only by the primary sequence of the CDR itself but also by a small number of nearby "Vernier zone" residues that contribute to shaping CDR structure (Foote et al., 1992). Scaffolds for CDR grafting were generated by modifying human framework regions at the few positions necessary to achieve identity with the Vernier zone residues of the corresponding chicken $V_H$ or $V_\lambda$ region. The framework scaffolds thereby generated were 94-96% identical to human framework sequences, making immunogenicity very unlikely. The first two N-terminal residues of the light chains were also eliminated, as these residues were situated proximal to CDR1 in mammalian antibodies and could in principle interfere with interaction of the antibodies with antigens. The CDRs of the chicken mAb were then grafted to the modified scaffolds, to create the humanized $V_H$ and $V_\lambda$ regions (FIG. 5C). Comparisons of apparent binding affinities of the chicken and humanized versions of the anti-FZD10 mAb showed that humanization was achieved without loss of affinity (FIG. 5D). This facile humanization contrasted with murine antibodies, which require considerable empirical optimization.

The above-described results showed that the DTLacO-2 platform permitted rapid ex vivo discovery of mAbs that recognized highly conserved targets. The power of the DTLacO platform was demonstrated by generating specific and high affinity mAbs to five cell surface antigens of therapeutic interest, the receptor tyrosine kinases VEGFR2 and TIE2, the glycoprotein TROP2, and the G protein-coupled receptor FZD10, all of which as described herein were obtained using DTLacO-2, and also the small TNF receptor family member FN14 obtained using DTLacO-1. The highly conserved extracellular domains of these cell surface receptors were likely to make them difficult targets for in vivo mAb discovery, which is limited by immune tolerance. The time from initial selection to identification of a high-affinity mAb (<10 nM) was on the order of 4-8 weeks, and subnanomolar affinity was achieved in 8-12 weeks. This timeframe for production of high affinity antibodies of desired specificity compared very favorably with other ex vivo or in vivo platforms for mAb discovery.

The DTLacO ex vivo mAb discovery platform provided several additional advantages relative to other mAb discovery approaches. The cells produced intact antibodies, which could be tested immediately for desired properties, whereas many in vitro approaches like the phage-display system produce single-chain antibodies, which are frequently difficult to convert to active full-length mAbs due to aggregation or instability. The DTLacO cells diversified Ig V regions using physiological pathways (somatic hypermutation and gene conversion), which target mutations mainly to CDRs, the subdomains of V regions that directly contact antigens. Furthermore, the cells proliferated rapidly and they were immortal, so that at each step of selection the cell population provided not only a renewable source of antibodies (or $V_H$ and $V_L$ sequences for expression of recombinant antibodies), but also a starting point for further optimization.

The DTLacO platform was distinguished from other mAb discovery platforms that use DT40 cells (Cumbers et al., 2002; Seo et al., 2005) by the ability to access both of the described physiological diversification mechanisms, somatic hypermutation and gene conversion. DTLacO cells also retained the ability to carry out homologous gene targeting, which permitted additional genetic engineering. The above feature of DTLacO cells was further exploited by substituting the endogenous $V_H$ region with a rearranged $V_H$ library, to create the DTLacO-2 population carrying an expanded $V_H$ repertoire. The third heavy chain CDR, CDR-H3, included the VDJ junction and was a major determinant for antigen recognition (Xu et al., 2000). CDR-H3 diversity may have contributed to the rapid selection of a high affinity anti-FZD10 mAb from the DTLacO-2 population. It is also possible to swap human V regions for chicken V regions (data not shown), which permitted optimizing affinity or functionality of mAbs discovered by other methods, as well as direct discovery of human therapeutic mAbs.

The chicken mAbs optimized in DTLacO cells proved to be readily humanized by CDR grafting into consensus human $V_H$ subgroup III and $V_\lambda$ subgroup III framework regions in which Vernier zone residues had been modified to preserve CDR structure. Humanization of Igs was carried out without loss of affinity, and achieved >94% identity to human Igs within the framework regions. This result was comparable to or better than many humanized murine mAbs now in the clinic, and made immunogenicity very unlikely. The readiness with which the mAbs were humanized contrasted with antibodies discovered in mice or murine cells, which must undergo empirical optimization. $V_H$ subgroup III and $V_\lambda$ subgroup III framework regions are conserved among a number of vertebrates, raising the possibility that mAb frameworks could be modified for treatment of chronic illness in other species.

REFERENCES

1. Kohler G, Milstein C (1975) Continuous cultures of fused cells secreting antibody of predefined specificity. Nature 256: 495-497.
2. Chiarella P, Fazio V M (2008) Mouse monoclonal antibodies in biological research: strategies for high-throughput production. Biotechnol Lett 30: 1303-1310.
3. Winter G, Griffiths A D, Hawkins R E, Hoogenboom H R (1994) Making antibodies by phage display technology. Annu Rev Immunol 12: 433-455.

4. Bratkovic T (2010) Progress in phage display: evolution of the technique and its application. Cell Mol Life Sci 67: 749-767.
5. Grandea A G, 3rd, Olsen O A, Cox T C, Renshaw M, Hammond P W, et al. (2010) Human antibodies reveal a protective epitope that is highly conserved among human and nonhuman influenza A viruses. Proc Natl Acad Sci USA 107: 12658-12663.
6. Hammond P W (2010) Accessing the human repertoire for broadly neutralizing HIV antibodies. MAbs 2: 157-164.
7. Cumbers S J, Williams G T, Davies S L, Grenfell R L, Takeda S, et al. (2002) Generation and iterative affinity maturation of antibodies in vitro using hypermutating B-cell lines. Nat Biotechnol 20: 1129-1134.
8. Seo H, Masuoka M, Murofushi H, Takeda S, Shibata T, et al. (2005) Rapid generation of specific antibodies by enhanced homologous recombination. Nat Biotechnol 23: 731-735.
9. Maizels N (2005) Immunoglobulin gene diversification. Annu Rev Genet. 39: 23-46.
10. Buerstedde J M, Takeda S (1991) Increased ratio of targeted to random integration after transfection of chicken B cell lines. Cell 67: 179-188.
11. Cummings W J, Yabuki M, Ordinario E C, Bednarski D W, Quay S, et al. (2007) Chromatin structure regulates gene conversion. PLoS Biol 5: e246.
12. Cummings W J, Bednarski D W, Maizels N (2008) Genetic variation stimulated by epigenetic modification. PLoS ONE 3: e4075.
13. Yabuki M, Ordinario E C, Cummings W J, Fujii M M, Maizels N (2009) E2A acts in cis in G1 phase of cell cycle to promote Ig gene diversification. J Immunol 182: 408-415.
14. Reynaud C A, Anquez V, Grimal H, Weill J C (1987) A hyperconversion mechanism generates the chicken light chain preimmune repertoire. Cell 48: 379-388.
15. Reynaud C A, Dahan A, Anquez V, Weill J C (1989) Somatic hyperconversion diversifies the single VH gene of the chicken with a high incidence in the D region. Cell 59: 171-183.
16. Huang Z, Cheng L, Guryanova O A, Wu Q, Bao S (2010) Cancer stem cells in glioblastoma—molecular signaling and therapeutic targeting. Protein Cell 1: 638-655.
17. Ferrara N (2010) Pathways mediating VEGF-independent tumor angiogenesis. Cytokine Growth Factor Rev 21: 21-26.
18. Cubas R, Zhang S, Li M, Chen C, Yao Q (2010) Trop2 expression contributes to tumor pathogenesis by activating the ERK MAPK pathway. Mol Cancer 9: 253.
19. Winkles J A (2008) The TWEAK-Fn14 cytokine-receptor axis: discovery, biology and therapeutic targeting. Nat Rev Drug Discov 7: 411-425.
20. Katoh M (2007) Networking of WNT, FGF, Notch, BMP, and Hedgehog signaling pathways during carcinogenesis. Stem Cell Rev 3: 30-38.
21. Almagro J C, Fransson J (2008) Humanization of antibodies. Front Biosci 13: 1619-1633.
22. Tsurushita N, Park M, Pakabunto K, Ong K, Avdalovic A, et al. (2004) Humanization of a chicken anti-IL-12 monoclonal antibody. J Immunol Methods 295: 9-19.
23. Nishibori N, Horiuchi H, Furusawa S, Matsuda H (2006) Humanization of chicken monoclonal antibody using phage-display system. Mol Immunol 43: 634-642.
24. Foote J, Winter G (1992) Antibody framework residues affecting the conformation of the hypervariable loops. J Mol Biol 224: 487-499.
25. Xu J L, Davis M M (2000) Diversity in the CDR3 region of VH is sufficient for most antibody specificities. Immunity 13: 37-45.
26. Yabuki M, Fujii M M, Maizels N (2005) The MRE11-RAD50-NBS1 complex accelerates somatic hypermutation and gene conversion of immunoglobulin variable regions. Nat Immunol 6: 730-736.
27. Robinett C C, Straight A, Li G, Willhelm C, Sudlow G, et al. (1996) In vivo localization of DNA sequences and visualization of large-scale chromatin organization using lac operator/repressor recognition. J Cell Biol 135: 1685-1700.
28. Sale J E, Calandrini D M, Takata M, Takeda S, Neuberger M S (2001) Ablation of XRCC2/3 transforms immunoglobulin V gene conversion into somatic hypermutation. Nature 412: 921-926.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A recombinant polynucleotide vector for integrating a target gene into a chicken immunoglobulin gene heavy chain locus, comprising:
   (a) a chicken immunoglobulin $V_H$ gene upstream nucleic acid sequence region comprising a sequence homologous to the 5' side of the start codon of endogenous genomic DNA encoding a chicken immunoglobulin $V_H$ gene;
   (b) a target gene that comprises a rearranged chicken immunoglobulin $V_H$-D-$J_H$ gene that has been isolated from a $V_H$ library of already rearranged $V_H$-D-$J_H$ regions isolated from a population of chicken bursa of Fabricius cells, wherein said $V_H$-D-$J_H$ gene is rearranged such that the $V_H$, D and $J_H$ genes are joined together; and
   (c) a chicken immunoglobulin $J_H$ gene downstream nucleic acid sequence region comprising a sequence homologous to the 3' side of the splice site of endogenous genomic DNA encoding a chicken immunoglobulin $J_H$ gene;

wherein the target gene, upon being integrated into the chicken immunoglobulin heavy chain locus of a DT40 cell, is capable of undergoing either or both of (i) somatic hypermutation in an immunoglobulin $V_H$ region-encoding sequence, and (ii) gene conversion between a rearranged chicken immunoglobulin $V_H$- encoding nucleic acid sequence and a DT40 $V_H$ pseudogene nucleic acid sequence.

2. The vector of claim 1, wherein the target gene further comprises a polynucleotide sequence that encodes a marker protein.

3. The vector of claim 2, wherein the marker protein is selected from green fluorescent protein (GFP) and blue fluorescent protein (BFP).

4. The vector of claim 1 wherein the somatic hypermutation takes place in either or both of an immunoglobulin $V_H$ complementarity determining region-encoding sequence and an immunoglobulin $V_H$ framework region-encoding sequence.

5. A composition comprising a plurality of recombinant polynucleotide vectors for integrating a plurality of target genes into a plurality of chicken immunoglobulin gene heavy chain loci, each of said vectors comprising:
(a) a chicken immunoglobulin $V_H$ gene upstream nucleic acid sequence region comprising a sequence homologous to the 5' side of the start codon of endogenous genomic DNA encoding a chicken immunoglobulin $V_H$ gene;
(b) a target gene that comprises a rearranged chicken immunoglobulin $V_H$-D-$J_H$ gene that has been isolated from a $V_H$ library of already rearranged $V_H$-D-$J_H$ regions derived isolated from a population of chicken bursa of Fabricius cells, wherein said $V_H$-D-$J_H$ gene is rearranged such that the $V_H$, D and $J_H$ genes are joined together; and
(c) a chicken immunoglobulin $J_H$ gene downstream nucleic acid sequence region comprising a sequence homologous to the 3' side of the splice site of endogenous genomic DNA encoding a chicken immunoglobulin $J_H$ gene,
wherein the target gene, upon being integrated into the chicken immunoglobulin heavy chain locus of a DT40 cell, is capable of undergoing either or both of (i) somatic hypermutation in an immunoglobulin $V_H$ region-encoding sequence, and (ii) gene conversion between the rearranged chicken immunoglobulin $V_H$- encoding nucleic acid sequence and a DT40 $V_H$ pseudogene nucleic acid sequence.

6. The composition of claim 5, wherein the target gene further comprises a polynucleotide sequence that encodes a marker protein.

7. The composition of claim 6, wherein the marker protein is selected from green fluorescent protein (GFP) and blue fluorescent protein (BFP).

8. The composition of claim 5 wherein the somatic hypermutation takes place in either or both of an immunoglobulin $V_H$ complementarity determining region-encoding sequence and an immunoglobulin Vu framework region-encoding sequence.

9. A composition, comprising:
(a) the vector of claim 1; and
(b) a second vector for integrating a second target gene into an immunoglobulin gene light chain locus, the second vector comprising
(1) a chicken immunoglobulin $V_L$ gene upstream nucleic acid sequence region comprising a sequence homologous to the 5' side of the start codon of endogenous genomic DNA encoding a chicken immunoglobulin $V_L$ gene;
(2) a second target gene that comprises a rearranged chicken immunoglobulin $V_L$-$J_L$ gene that has been isolated from a population of chicken bursa of Fabricius cells; and
(3) a chicken immunoglobulin $J_L$ gene downstream nucleic acid sequence region comprising a sequence homologous to the 3' side of the splice site of endogenous genomic DNA encoding a chicken immunoglobulin $J_L$ gene,
wherein the second target gene, upon being integrated into the chicken immunoglobulin light chain locus of a DT40 cell, is capable of undergoing either or both of (i) somatic hypermutation in an immunoglobulin $V_L$ region-encoding sequence, and (ii) gene conversion between a rearranged chicken immunoglobulin $V_L$- encoding nucleic acid sequence and a DT40 $V_L$ pseudogene nucleic acid sequence.

10. A composition, comprising:
(1) the composition of claim 5; and
(2) one or a plurality of recombinant polynucleotide vectors for integrating a plurality of target genes into a plurality of chicken immunoglobulin gene light chain loci, each of said vectors comprising:
(a) a chicken immunoglobulin $V_L$ gene upstream nucleic acid sequence region comprising a sequence homologous to the 5' side of the start codon of endogenous genomic DNA encoding a chicken immunoglobulin $V_L$ gene;
(b) a second target gene that comprises a rearranged chicken immunoglobulin $V_L$-$J_L$ gene that has been isolated from a population of chicken bursa of Fabricius cells; and
(c) a chicken immunoglobulin $J_L$ gene downstream nucleic acid sequence region comprising a sequence homologous to the 3' side of the splice site of endogenous genomic DNA encoding a chicken immunoglobulin $J_L$ gene,
wherein the second target gene, upon being integrated into the chicken immunoglobulin light chain locus of a DT40 cell, is capable of undergoing either or both of (i) somatic hypermutation in an immunoglobulin $V_L$ region-encoding sequence, and (ii) gene conversion between a rearranged chicken immunoglobulin $V_L$- encoding nucleic acid sequence and a DT40 $V_L$ pseudogene nucleic acid sequence, and
wherein the rearranged chicken immunoglobulin $V_L$-$J_L$ gene is obtained from a plurality of isolated rearranged chicken immunoglobulin $V_L$-$J_L$ genes from a population of chicken bursa of Fabricius cells.

11. The composition of claim 9, wherein the second target gene further comprises a polynucleotide sequence that encodes a second marker protein.

12. The composition of claim 11, wherein the second marker protein is selected from green fluorescent protein (GFP) and blue fluorescent protein (BFP).

13. The composition of claim 9 wherein the somatic hypermutation takes place in either or both of an immunoglobulin $V_L$ complementarity determining region-encoding sequence and an immunoglobulin $V_L$ framework region-encoding sequence.

14. A host cell, comprising the vector of claim 1.

15. The host cell of claim 14 wherein the cell is a bacterial cell.

16. The host cell of claim 14 wherein the cell is a chicken cell.

17. The host cell of claim 14 wherein the cell is a chicken bursal lymphoma cell.

18. The host cell of claim 14 wherein the cell is a DT40 cell.

19. The host cell of claim 16 wherein the immunoglobulin gene heavy chain locus in the host cell comprises a polymerized lactose operator.

20. The host cell of claim 16 wherein the immunoglobulin gene light chain locus in the host cell comprises a polymerized lactose operator.

21. A library of host cells according to claim 14.

22. A method for integrating a target gene into a chicken immunoglobulin heavy chain locus, comprising:
   (a) transfecting chicken B-cells with the vector of claim 1; and
   (b) identifying a chicken B-cell in which the target gene is integrated into the immunoglobulin heavy chain locus.

23. A method for integrating a first target gene into a chicken immunoglobulin heavy chain locus and integrating a second target gene into an immunoglobulin light chain locus, comprising:
   (a) transfecting one or a plurality of chicken B-cells with the composition of claim 9 to obtain one or a plurality of transfected B-cells; and
   (b) identifying a transfected chicken B-cell from (a) in which the target gene that comprises a rearranged chicken immunoglobulin $V_H$-D-$J_H$ gene is integrated into the immunoglobulin gene heavy chain locus and the second target gene is integrated into the immunoglobulin gene light chain locus.

24. A method for producing a repertoire of chicken immunoglobulin heavy chain polypeptide sequence variants of a target polypeptide that is encoded by a target gene that comprises a rearranged chicken immunoglobulin $V_H$-D-$J_H$ gene, comprising:
   culturing a chicken B-cell containing the vector of claim 1 under conditions that allow for proliferation of the B-cell until a plurality of B-cells is obtained, wherein the B-cell is capable of either or both of (i) somatic hypermutation in an immunoglobulin $V_H$ complementarity determining region-encoding sequence, and (ii) gene conversion between a rearranged chicken immunoglobulin $V_H$-encoding nucleic acid sequence and a $V_H$ pseudogene nucleic acid sequence, and thereby producing a repertoire of chicken immunoglobulin heavy chain polypeptide sequence variants of the target polypeptide.

25. The method of claim 24 wherein the chicken B-cell further comprises a second vector for integrating a second target gene into a chicken immunoglobulin gene light chain locus, the second vector comprising
   (a) a chicken immunoglobulin $V_L$ gene upstream nucleic acid sequence region comprising a sequence homologous to the 5' side of the start codon of endogenous genomic DNA encoding a chicken immunoglobulin $V_L$ gene;
   (b) a second target gene that comprises a rearranged chicken immunoglobulin $V_L$-$J_L$ gene that has been isolated from a population of chicken bursa of Fabricius cells; and
   (c) a chicken immunoglobulin $J_L$ gene downstream nucleic acid sequence region comprising a sequence homologous to the 3' side of the splice site of endogenous genomic DNA encoding a chicken immunoglobulin $J_L$ gene,
   wherein the second target gene, upon being integrated into the chicken immunoglobulin light chain locus of a DT40 cell, is capable of undergoing either or both of (i) somatic hypermutation in an immunoglobulin $V_L$ complementarity determining region-encoding sequence, and (ii) gene conversion between a rearranged chicken immunoglobulin $V_L$-encoding nucleic acid sequence and a DT40 $V_L$ pseudogene nucleic acid sequence.

26. The method of claim 25, wherein the chicken immunoglobulin gene light chain locus comprises a polymerized lactose operator.

27. The method of claim 22 wherein the chicken cell is selected from DT40 and DTLacO.

28. The method of claim 25, further comprising screening the plurality of chicken B-cells for binding to an antigen.

* * * * *

UNITED STATES PATENT AND TRADEMARK OFFICE
CERTIFICATE OF CORRECTION

PATENT NO. : 9,677,070 B2  
APPLICATION NO. : 13/802255  
DATED : June 13, 2017  
INVENTOR(S) : Daniel S. Allison et al.

Page 1 of 1

It is certified that error appears in the above-identified patent and that said Letters Patent is hereby corrected as shown below:

In the Specification

| Column | Line | Error |
|---|---|---|
| 13 | 60 | "complementartity" should read --complementarity-- |
| 14 | 60 | "complementartity" should read --complementarity-- |
| 15 | 2 | "complementartity" should read --complementarity-- |
| 17 | 35 | "complementartity" should read --complementarity-- |
| 19 | 2 | "Ill" should read --Ill-- |
| 25 | 15 | "IgA" should read --Igλ-- |
| 27 | 56 | "complementartity" should read --complementarity-- |
| 31 | 65 | "22- and 1.8-kb" should read --2.2- and 1.8-kb-- |
| 32 | 1 | "5-CCGT-" should read --5'-CCGT- -- |
| 32 | 15 | "SEC) ID" should read --SEQ ID-- |
| 32 | 51 | "FLAGA" should read --FLAGλ-- |
| 33 | 1 | "GTTCCGTTCCGGTATG-3'" should read --GTTCCGTTTCCGGTATG-3'-- |
| 33 | 65 | "5-GCG-" should read --5'-GCG- -- |
| 35 | 19 | "IgA" should read --Igλ-- |
| 35 | 21 | "IgA" should read --Igλ-- |
| 59 | 32 | "regions derived isolated" should read --regions isolated-- |

In the Claims

| | | |
|---|---|---|
| 59 | 58 | "Vu" should read --$V_H$-- |

Signed and Sealed this  
Twenty-third Day of January, 2018

Joseph Matal  
*Performing the Functions and Duties of the  
Under Secretary of Commerce for Intellectual Property and  
Director of the United States Patent and Trademark Office*

SEQUENCE LISTING

```
<160> NUMBER OF SEQ ID NOS: 42

<210> SEQ ID NO 1
<211> LENGTH: 28
<212> TYPE: DNA
<213> ORGANISM: Artificial Sequence
<220> FEATURE:
<223> OTHER INFORMATION: Primer sequence

<400> SEQUENCE: 1
ggggtctcta tggggtctaa gcgtggcc                                           28

<210> SEQ ID NO 2
```

```
<211> LENGTH: 34
<212> TYPE: DNA
<213> ORGANISM: Artificial Sequence
<220> FEATURE:
<223> OTHER INFORMATION: Primer sequence

<400> SEQUENCE: 2
ggccgattct tttctcatga gatccctcca gaag                            34

<210> SEQ ID NO 3
<211> LENGTH: 30
<212> TYPE: DNA
<213> ORGANISM: Artificial Sequence
<220> FEATURE:
<223> OTHER INFORMATION: Primer sequence

<400> SEQUENCE: 3
ttccccacaa ccaggccatg cgcctccttg                                 30

<210> SEQ ID NO 4
<211> LENGTH: 28
<212> TYPE: DNA
<213> ORGANISM: Artificial Sequence
<220> FEATURE:
<223> OTHER INFORMATION: Primer sequence

<400> SEQUENCE: 4
cctgcagaca cccagaggag ggctcagc                                   28

<210> SEQ ID NO 5
<211> LENGTH: 40
<212> TYPE: DNA
<213> ORGANISM: Artificial Sequence
<220> FEATURE:
<223> OTHER INFORMATION: Primer sequence

<400> SEQUENCE: 5
tgaatgcttt gttagcccta attagggatt gaattgagag                      40

<210> SEQ ID NO 6
<211> LENGTH: 21
<212> TYPE: DNA
<213> ORGANISM: Artificial Sequence
<220> FEATURE:
<223> OTHER INFORMATION: Primer sequence

<400> SEQUENCE: 6
ccgtgagacc ccccgttgac c                                          21

<210> SEQ ID NO 7
<211> LENGTH: 30
<212> TYPE: DNA
<213> ORGANISM: Artificial Sequence
<220> FEATURE:
<223> OTHER INFORMATION: Primer sequence

<400> SEQUENCE: 7
gcccgaccga agtcatcgtc tcctccggtg                                 30

<210> SEQ ID NO 8
<211> LENGTH: 20
<212> TYPE: DNA
<213> ORGANISM: Artificial Sequence
<220> FEATURE:
<223> OTHER INFORMATION: Primer sequence

<400> SEQUENCE: 8
```
tttgccttca aatcacccta                                        20

<210> SEQ ID NO 9
<211> LENGTH: 21
<212> TYPE: DNA
<213> ORGANISM: Artificial Sequence
<220> FEATURE:
<223> OTHER INFORMATION: Primer sequence

<400> SEQUENCE: 9
gggtctgcgg gctctatggg g                                      21

<210> SEQ ID NO 10
<211> LENGTH: 21
<212> TYPE: DNA
<213> ORGANISM: Artificial Sequence
<220> FEATURE:
<223> OTHER INFORMATION: Primer sequence

<400> SEQUENCE: 10
atcgccgcgg caattttggg g                                      21

<210> SEQ ID NO 11
<211> LENGTH: 31
<212> TYPE: DNA
<213> ORGANISM: Artificial Sequence
<220> FEATURE:
<223> OTHER INFORMATION: Primer sequence

<400> SEQUENCE: 11
caggagctcg cggggccgtc actgattgcc g                           31

<210> SEQ ID NO 12
<211> LENGTH: 34
<212> TYPE: DNA
<213> ORGANISM: Artificial Sequence
<220> FEATURE:
<223> OTHER INFORMATION: Primer sequence

<400> SEQUENCE: 12
gcgcaagctt ccccagcctg ccgccaagtc caag                        34

<210> SEQ ID NO 13
<211> LENGTH: 21
<212> TYPE: DNA
<213> ORGANISM: Artificial Sequence
<220> FEATURE:
<223> OTHER INFORMATION: Primer sequence

<400> SEQUENCE: 13
gggtctgcgg gctctatggg g                                      21

<210> SEQ ID NO 14
<211> LENGTH: 21
<212> TYPE: DNA
<213> ORGANISM: Artificial Sequence
<220> FEATURE:
<223> OTHER INFORMATION: Primer sequence

<400> SEQUENCE: 14
atcgccgcgg caattttggg g                                      21

<210> SEQ ID NO 15
<211> LENGTH: 30
<212> TYPE: DNA

```
<213> ORGANISM: Artificial Sequence
<220> FEATURE:
<223> OTHER INFORMATION: Primer sequence

<400> SEQUENCE: 15
tcactgattg ccgttttctc ccctctctcc                                          30

<210> SEQ ID NO 16
<211> LENGTH: 21
<212> TYPE: DNA
<213> ORGANISM: Artificial Sequence
<220> FEATURE:
<223> OTHER INFORMATION: Primer sequence

<400> SEQUENCE: 16
ggtcaacggg gggtctcacg g                                                   21

<210> SEQ ID NO 17
<211> LENGTH: 101
<212> TYPE: PRT
<213> ORGANISM: Gallus gallus

<400> SEQUENCE: 17

Ala Val Thr Leu Asp Glu Ser Gly Gly Gly Leu Gln Thr Pro Gly Arg
1               5                   10                  15

Ala Leu Ser Leu Val Cys Lys Ala Ser Gly Phe Thr Phe Ser Ser Tyr
            20                  25                  30

Asn Met Gly Trp Val Arg Gln Ala Pro Gly Lys Gly Leu Glu Phe Val
        35                  40                  45

Ala Gly Ile Asp Asn Thr Gly Arg Tyr Thr Gly Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Ala Ala Gly
            100

<210> SEQ ID NO 18
<211> LENGTH: 101
<212> TYPE: PRT
<213> ORGANISM: Gallus gallus

<400> SEQUENCE: 18

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Gly Ser Gly Thr Arg Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Thr Lys Cys Ala Tyr
            100
```

```
<210> SEQ ID NO 19
<211> LENGTH: 94
<212> TYPE: PRT
<213> ORGANISM: Gallus gallus

<400> SEQUENCE: 19

Ala Leu Thr Gln Pro Ser Ser Val Ser Ala Asn Pro Gly Gly Thr Val
1               5                   10                  15

Lys Ile Thr Cys Ser Gly Asp Ser Ser Tyr Tyr Gly Trp Tyr Gln Gln
            20                  25                  30

Lys Ala Pro Gly Ser Ala Pro Val Thr Val Ile Tyr Asp Asn Thr Asn
        35                  40                  45

Arg Pro Ser Asn Ile Pro Ser Arg Phe Ser Gly Ser Lys Ser Gly Ser
    50                  55                  60

Thr Ala Thr Leu Thr Ile Thr Gly Val Arg Ala Asp Asp Asn Ala Val
65                  70                  75                  80

Tyr Tyr Cys Ala Ser Thr Asp Ser Ser Ser Thr Ala Ala Arg
                85                  90

<210> SEQ ID NO 20
<211> LENGTH: 112
<212> TYPE: PRT
<213> ORGANISM: Gallus gallus

<400> SEQUENCE: 20

Ala Leu Thr Gln Pro Ala Ser Val Ser Ala Asn Pro Gly Glu Thr Val
1               5                   10                  15

Lys Ile Thr Cys Ser Gly Gly Gly Ser Tyr Ala Gly Ser Tyr Tyr Tyr
            20                  25                  30

Gly Trp Tyr Gln Gln Lys Tyr Ala Gly Ser Tyr Tyr Tyr Gly Trp Tyr
        35                  40                  45

Gln Gln Lys Ser Pro Gly Ser Ala Pro Val Thr Leu Ile Tyr Asn Asn
    50                  55                  60

Asn Asn Arg Pro Ser Asp Ile Pro Ser Arg Phe Ser Gly Ser Lys Ser
65                  70                  75                  80

Gly Ser Thr Ala Thr Leu Thr Ile Thr Gly Val Arg Ala Asp Asp Glu
                85                  90                  95

Ala Val Tyr Phe Cys Gly Ser Ala Asp Asn Ser Gly Ala Ala Phe Gly
            100                 105                 110

<210> SEQ ID NO 21
<211> LENGTH: 23
<212> TYPE: DNA
<213> ORGANISM: Artificial Sequence
<220> FEATURE:
<223> OTHER INFORMATION: Primer sequence

<400> SEQUENCE: 21
gggacacctg aaggcatgag tgg                                         23

<210> SEQ ID NO 22
<211> LENGTH: 22
<212> TYPE: DNA
<213> ORGANISM: Artificial Sequence
<220> FEATURE:
<223> OTHER INFORMATION: Primer sequence

<400> SEQUENCE: 22
ggcggaatcc cagcagctgt gt                                          22
```

```
<210> SEQ ID NO 23
<211> LENGTH: 25
<212> TYPE: DNA
<213> ORGANISM: Artificial Sequence
<220> FEATURE:
<223> OTHER INFORMATION: Primer sequence

<400> SEQUENCE: 23
gtgagtcgct gacctcgtct cggtc                                             25

<210> SEQ ID NO 24
<211> LENGTH: 25
<212> TYPE: DNA
<213> ORGANISM: Artificial Sequence
<220> FEATURE:
<223> OTHER INFORMATION: Primer sequence

<400> SEQUENCE: 24
gggctctttc tacctcaagg catgt                                             25

<210> SEQ ID NO 25
<211> LENGTH: 5
<212> TYPE: PRT
<213> ORGANISM: Artificial Sequence
<220> FEATURE:
<223> OTHER INFORMATION: FLAG tag sequence

<400> SEQUENCE: 25

Asp Tyr Lys Asp Glu
1               5

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide amplification primer

<400> SEQUENCE: 26
agcctcatta tccccctgat                                                   20

<210> SEQ ID NO 27
<211> LENGTH: 20
<212> TYPE: DNA
<213> ORGANISM: Artificial Sequence
<220> FEATURE:
<223> OTHER INFORMATION: Oligonucleotide amplification primer

<400> SEQUENCE: 27
tctctttccc ttcgctttga                                                   20

<210> SEQ ID NO 28
<211> LENGTH: 20
<212> TYPE: DNA
<213> ORGANISM: Artificial Sequence
<220> FEATURE:
<223> OTHER INFORMATION: Oligonucleotide amplification primer

<400> SEQUENCE: 28
acagttccgt ttccggtatg                                                   20

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide amplification primer
```

<400> SEQUENCE: 29
cactccatcc tcttgctggt                                                  20

<210> SEQ ID NO 30
<211> LENGTH: 8
<212> TYPE: PRT
<213> ORGANISM: Artificial Sequence
<220> FEATURE:
<223> OTHER INFORMATION: FLAG-tag sequence

<400> SEQUENCE: 30

Asp Tyr Lys Asp Asp Asp Asp Lys
1               5

<210> SEQ ID NO 31
<211> LENGTH: 7
<212> TYPE: PRT
<213> ORGANISM: Artificial Sequence
<220> FEATURE:
<223> OTHER INFORMATION: tabacoo etch virus (TEV) cysteine protease
      recognition site

<400> SEQUENCE: 31

Glu Asn Leu Tyr Phe Gln Gly
1               5

<210> SEQ ID NO 32
<211> LENGTH: 1548
<212> TYPE: DNA
<213> ORGANISM: Artificial Sequence
<220> FEATURE:
<223> OTHER INFORMATION: Construct encoding chimeric chicken-human Ig
      heavy chain

<400> SEQUENCE: 32
gccgtgacgt tggacgagtc cggggggcggc ctccagacgc ccggggggagc gctcagcctc         60 gtctgcaagg cctccgggtt caccttcagc agtaacgcca tgggttgggt gcgacaggcg         120
cccggcaagg ggctggagtg ggtcgctggt attgatgatg atggtagtgg cacaagatac         180
gcgccggcgg tgaagggccg tgccaccatc tcgaggggaca cgggcagag cacactgagg         240 ctgcagctga caacctcag ggctgaggac accggcatct actactgcac gaaatgtgct         300
tacagtagtg gttgtgatta tgaagctggt tatatcgacg catggggcca cgggaccgaa         360
gtcatcgtct cctccgcctc gaccaagggc ccatcggtct tccccctggc accctcctcc         420
aagagcacct ctggggggcac agcggccctg ggctgcctgg tcaaggacta cttccccgaa         480
ccggtgacgg tgtcgtggaa ctcaggcgcc ctgaccagcg gcgtgcacac cttcccggct         540
gtcctacagt cctcaggact ctactccctc agcagcgtgg tgaccgtgcc ctccagcagc         600
ttgggcaccc agacctacat ctgcaacgtg aatcacaagc ccagcaacac caaggtggac         660
aagaaagttg agcccaaatc ttgtgacaaa actcacacat gcccaccgtg cccagcacct         720
gaactcctgg ggggaccgtc agtcttcctc ttccccccaa aacccaagga caccctcatg         780
atctcccgga cccctgaggt cacatgcgtg gtggtggacg tgagccacga agaccctgag         840
gtcaagttca actggtacgt ggacggcgtg gaggtgcata atgccaagac aaagccgcgg         900
gaggagcagt acaacagcac gtaccgtgtg gtcagcgtcc tcaccgtcct gcaccaggac         960
tggctgaatg gcaaggagta caagtgcaag gtctccaaca aagccctccc agcccccatc        1020
gagaaaacca tctccaaagc caaagggcag ccccgagaac cacaggtgta cacctgcgcc        1080

```
ccatcccggg atgagctgac caagaaccag gtcagcctga cctgcctggt caaaggcttc    1140
tatcccagcg acatcgccgt ggagtgggag agcaatgggc agccggagaa caactacaag    1200
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacacagaa gagcctctcc ctgtctccgg gtaaagatta caaggatgac    1380
gacgataagg agaacctgta ttttcagggt gatctcctcc attggcctct ggaggccgaa    1440
gaggacgacg acatccaacg cctttgggcc accacctcca ccttcatcgt cctcttcatc    1500
ctcagcctct tctacagcgc caccgtcacc ctcatcaagg tgaaatga              1548
```

```
<210> SEQ ID NO 33
<211> LENGTH: 43
<212> TYPE: DNA
<213> ORGANISM: Artificial Sequence
<220> FEATURE:
<223> OTHER INFORMATION: Construct encoding rearranged chicken IgH J
      region (chVDJ)

<400> SEQUENCE: 33
```

```
atcgacgcat ggggccacgg gaccgaagtc atcgtctcct ccg                       43
```

```
<210> SEQ ID NO 34
<211> LENGTH: 989
<212> TYPE: DNA
<213> ORGANISM: Artificial Sequence
<220> FEATURE:
<223> OTHER INFORMATION: Construct encoding human Ig C-gamma 1 region

<400> SEQUENCE: 34
```

```
cctcgaccaa gggcccatcg gtcttccccc tggcaccctc ctccaagagc acctctgggg     60
gcacagcggc cctgggctgc ctggtcaagg actacttccc cgaaccggtg acggtgtcgt    120
ggaactcagg cgccctgacc agcggcgtgc acaccttccc ggctgtccta cagtcctcag    180
gactctactc cctcagcagc gtggtgaccg tgccctccag cagcttgggc acccagacct    240
acatctgcaa cgtgaatcac aagcccagca acaccaaggt ggacaagaaa gttgagccca    300
aatcttgtga caaaactcac acatgcccac cgtgcccagc acctgaactc ctggggggac    360
cgtcagtctt cctcttcccc ccaaaaccca aggacaccct catgatctcc cggacccctg    420
aggtcacatg cgtggtggtg gacgtgagcc acgaagaccc tgaggtcaag ttcaactggt    480
acgtggacgg cgtggaggtg cataatgcca agacaaagcc gcgggaggag cagtacaaca    540
gcacgtaccg tgtggtcagc gtcctcaccg tcctgcacca ggactggctg aatggcaagg    600
agtacaagtg caaggtctcc aacaaagccc tcccagcccc catcgagaaa accatctcca    660
aagccaaagg gcagccccga gaaccacagg tgtacaccct gcccccatcc cgggatgagc    720
tgaccaagaa ccaggtcagc ctgacctgcc tggtcaaagg cttctatccc agcgacatcg    780
ccgtggagtg ggagagcaat gggcagccgg agaacaacta caagaccacg cctcccgtgc    840
tggactccga cggctccttc ttcctctaca gcaagctcac cgtggacaag agcaggtggc    900
agcaggggaa cgtcttctca tgctccgtga tgcatgaggc tctgcacaac cactacacac    960
agaagagcct ctccctgtct ccgggtaaa                                       989
```

```
<210> SEQ ID NO 35
<211> LENGTH: 24
<212> TYPE: DNA
<213> ORGANISM: Artificial Sequence
<220> FEATURE:
```

<223> OTHER INFORMATION: Construct encoding peptide epitope tag

<400> SEQUENCE: 35
gattacaagg atgacgacga taag                                           24

<210> SEQ ID NO 36
<211> LENGTH: 21
<212> TYPE: DNA
<213> ORGANISM: Artificial Sequence
<220> FEATURE:
<223> OTHER INFORMATION: Construct encoding protease cleavage site

<400> SEQUENCE: 36
gagaacctgt attttcaggg t                                              21

<210> SEQ ID NO 37
<211> LENGTH: 138
<212> TYPE: DNA
<213> ORGANISM: Artificial Sequence
<220> FEATURE:
<223> OTHER INFORMATION: Construct encoding artificial chicken IgH
      transmembrane domain

<400> SEQUENCE: 37
gatctcctcc attggcctct ggaggccgaa gaggacgacg acatccaacg cctttgggcc    60
accacctcca ccttcatcgt cctcttcatc ctcagcctct tctacagcgc caccgtcacc   120
ctcatcaagg tgaaatga                                                 138

<210> SEQ ID NO 38
<211> LENGTH: 376
<212> TYPE: DNA
<213> ORGANISM: Artificial Sequence
<220> FEATURE:
<223> OTHER INFORMATION: Construct encoding rearranged chicken IgH J
      region (chVDJ)

<400> SEQUENCE: 38
gccgtgacgt tggacgagtc cggggggcggc ctccagacgc cgggggagc gctcagcctc    60 gtctgcaagg cctccgggtt caccttcagc agtaacgcca tgggttgggt gcgacaggcg   120
cccggcaagg ggctggagtg ggtcgctggt attgatgatg atggtagtgg cacaagatac   180
gcgccggcgg tgaagggccg tgccaccatc tcgagggaca cgggcagag cacactgagg    240 ctgcagctga caaacctcag ggctgaggac accggcatct actactgcac gaaatgtgct   300
tacagtagtg gttgtgatta tgaagctggt tatatcgacg catggggcca cgggaccgaa   360
gtcatcgtct cctccg                                                   376

<210> SEQ ID NO 39
<211> LENGTH: 989
<212> TYPE: DNA
<213> ORGANISM: Artificial Sequence
<220> FEATURE:
<223> OTHER INFORMATION: Construct encoding human Ig C-gamma 1 region

<400> SEQUENCE: 39
cctcgaccaa gggcccatcg gtcttccccc tggcaccctc ctccaagagc acctctgggg    60
gcacagcggc cctgggctgc ctggtcaagg actacttccc cgaaccggtg acggtgtcgt   120
ggaactcagg cgccctgacc agcggcgtgc acaccttccc ggctgtccta cagtcctcag   180
gactctactc cctcagcagc gtggtgaccg tgccctccag cagcttgggc acccagacct   240
acatctgcaa cgtgaatcac aagcccagca acaccaaggt ggacaagaaa gttgagccca   300

```
aatcttgtga caaaactcac acatgcccac cgtgcccagc acctgaactc ctgggggac      360 cgtcagtctt cctcttcccc ccaaaaccca aggacaccct catgatctcc cggaccctg      420 aggtcacatg cgtggtggtg gacgtgagcc acgaagaccc tgaggtcaag ttcaactggt      480
acgtggacgg cgtggaggtg cataatgcca agacaaagcc gcgggaggag cagtacaaca      540
gcacgtaccg tgtggtcagc gtcctcaccg tcctgcacca ggactggctg aatggcaagg      600
agtacaagtg caaggtctcc aacaaagccc tcccagcccc catcgagaaa accatctcca      660
aagccaaagg gcagccccga gaaccacagg tgtacaccct gcccccatcc cgggatgagc      720
tgaccaagaa ccaggtcagc ctgacctgcc tggtcaaagg cttctatccc agcgacatcg      780
ccgtggagtg ggagagcaat gggcagccgg agaacaacta caagaccacg cctcccgtgc      840
tggactccga cggctccttc ttcctctaca gcaagctcac cgtggacaag agcaggtggc      900 agcagggaa cgtcttctca tgctccgtga tgcatgaggc tctgcacaac cactacacac      960
agaagagcct ctccctgtct ccgggtaaa                                       989
```

```
<210> SEQ ID NO 40
<211> LENGTH: 24
<212> TYPE: DNA
<213> ORGANISM: Artificial Sequence
<220> FEATURE:
<223> OTHER INFORMATION: Construct encoding peptide epitope tag

<400> SEQUENCE: 40
gattacaagg atgacgacga taag                                            24

<210> SEQ ID NO 41
<211> LENGTH: 21
<212> TYPE: DNA
<213> ORGANISM: Artificial Sequence
<220> FEATURE:
<223> OTHER INFORMATION: Construct encoding protease cleavage site

<400> SEQUENCE: 41
gagaacctgt attttcaggg t                                               21

<210> SEQ ID NO 42
<211> LENGTH: 138
<212> TYPE: DNA
<213> ORGANISM: Artificial Sequence
<220> FEATURE:
<223> OTHER INFORMATION: Construct encoding artificial chicken IgH
      transmembrane domain

<400> SEQUENCE: 42
gatctcctcc attggcctct ggaggccgaa gaggacgacg acatccaacg cctttgggcc      60
accacctcca ccttcatcgt cctcttcatc ctcagcctct tctacagcgc caccgtcacc     120
ctcatcaagg tgaaatga                                                  138
```